US009333241B2

(12) United States Patent
Kelly

(10) Patent No.: US 9,333,241 B2
(45) Date of Patent: May 10, 2016

(54) THYROID-STIMULATING HORMONE RECEPTOR POLYPEPTIDE AGONIST GLYCOFORMS TO TREAT METABOLIC SYNDROME

(75) Inventor: James D. Kelly, Mercer Island, WA (US)

(73) Assignee: LipoLytics Therapeutics, LLC, Mercer Island, WA (US)

( * ) Notice: Subject to any disclaimer, the term of this patent is extended or adjusted under 35 U.S.C. 154(b) by 0 days.

(21) Appl. No.: 12/707,334

(22) Filed: Feb. 17, 2010

(65) Prior Publication Data

US 2010/0210512 A1 Aug. 19, 2010

Related U.S. Application Data

(63) Continuation of application No. 12/158,796, filed as application No. PCT/US2006/048820 on Dec. 21, 2006, now abandoned.

(60) Provisional application No. 60/753,798, filed on Dec. 23, 2005.

(51) Int. Cl.
*A61K 38/24* (2006.01)
*A61K 38/22* (2006.01)

(52) U.S. Cl.
CPC .................................... *A61K 38/24* (2013.01)

(58) Field of Classification Search
None
See application file for complete search history.

(56) References Cited

U.S. PATENT DOCUMENTS

| | | | | |
|---|---|---|---|---|
| 5,840,566 | A | 11/1998 | Kourides et al. | 435/240.2 |
| 6,114,144 | A | 9/2000 | Kourides et al. | 435/69.4 |
| 6,365,127 | B1 | 4/2002 | Kourides et al. | 424/9.1 |
| 2003/0095983 | A1 | 5/2003 | Kelly et al. | 424/198.1 |
| 2003/0198596 | A1 | 10/2003 | Kourides et al. | 424/9.2 |
| 2003/0207403 | A1 | 11/2003 | Paszty et al. | 435/69.1 |
| 2004/0138113 | A1 | 7/2004 | Kelly et al. | 514/12 |
| 2004/0176294 | A1 | 9/2004 | Kelly | 514/12 |
| 2004/0266665 | A1 | 12/2004 | Weintraub et al. | 514/8 |
| 2005/0095676 | A1 | 5/2005 | El Tayar et al. | 435/69.1 |
| 2005/0096264 | A1 | 5/2005 | MacDonald et al. | 514/8 |
| 2005/0143564 | A1 | 6/2005 | Seki et al. | 530/380 |
| 2005/0158740 | A1 | 7/2005 | Shemesh et al. | 435/6 |
| 2005/0171017 | A1 | 8/2005 | Kelly et al. | 514/12 |
| 2005/0250185 | A1 | 11/2005 | Murphy et al. | 435/69.4 |
| 2005/0272635 | A1 | 12/2005 | Kelly | 514/2 |

FOREIGN PATENT DOCUMENTS

| | | | |
|---|---|---|---|
| EP | 1 971 361 | B1 | 6/2014 |
| JP | 5727693 | B2 | 4/2015 |
| WO | 01/73034 | | 10/2001 |
| WO | 03/006051 | | 1/2003 |
| WO | 2005/076013 | | 8/2005 |

OTHER PUBLICATIONS

Klok et al., The role of leptin and ghrelin in the regulation of food intake and body weight in humans: a review, Obesity Rev., 8:21-34, 2007.*

Gagnon et al., Thyroid-simtulating hormone stimulates lipolysis in adipocytes in culture and raises serum free fatty acid levels in vivo, Metab. Clin. Exp. 59:547-553, 2010.*

Xu et al., Thyroid stimulating hormone, independent of thyroid hormone, can elevate the serum total cholesterol level in patients with coronary heart diseases: a cross-sectional design, Nutrition Metab. 9:44, 2012.*

Reynisdottir et al., Multiple lipolysis defects in the insulin resistance (metabolic) syndrome, J. Clin. Invest. 93:2990-2999, Jun. 1994.*

Arch, "$\beta_3$-Adrenoceptor agonists: potential, pitfalls and progress," *European Journal of Pharmacology 440*:99-107, 2002.

Baenziger et al., "Circulatory half-life but not interaction with the lutropin/chorionic gonadotropin receptor is modulated by sulfation of bovine lutropin oligosaccharides," *Proc. Natl. Acad. Sci. USA 89*:334-338, 1992.

Baxter et al., "Bile acids heat things up," *Nature 439*:402-403, 2006.

Blaak et al., "Role of α- and β-adrenoceptors in sympathetically mediated thermogenesis," *Am. J. Physiol. 264*:E11-E17, 1993.

Buice et al., "Near-IR and IR Imaging in Lipid Metabolism and Obesity," *Cellular and Molecular Biology 44*(1):53-64, 1998.

Davies et al., "Thyrotropin Receptors in Human Fat," *N. Engl. J. Med. 296*(13):759, 1977.

Day et al., "Steatohepatitis: A Tale of Two "Hits"?," *Gastroenterology 114*(4):842-845, 1998.

de Souza et al., "Beta$_3$-Adrenoceptor Agonists as Anti-diabetic and Anti-obesity Drugs in Humans," *Current Pharmaceutical Design 7*:1433-1449, 2001.

Dias, "Is there any physiological role for gonadotrophin oligosaccharide heterogeneity in humans? II. A biochemical point of view," *Human Reproduction 16*(5):825-830, 2001.

Endo et al., "Cloning and Functional Expression of a Thyrotropin Receptor cDNA from Rat Fat Cells," *The Journal of Biological Chemistry 270*(18):10833-10837, 1995.

Galway et al., "In Vitro and in Vivo Bioactivity of Recombinant Human Follicle-Stimulating Hormone and Partially Deglycosylated Variants Secreted by Transfected Eukaryotic Cell Lines," *Endocrinology 127*(1):93-100, 1990.

Grossmann et al., "Novel Insights into the Molecular Mechanisms of Human Thyrotropin Action: Structural, Physiological, and Therapeutic Implications for the Glycoprotein Hormone Family," *Endocrine Reviews 18*(4):476-501, 1997.

Grossmann et al., "Expression of Biologically Active Human Thyrotropin (hTSH) in a Baculovirus System: Effect of Insect Cell Glycosylation on hTSH Activity in Vitro and in Vivo," *Endocrinology 138*(1):92-100, 1997.

Guan et al., "A futile metabolic cycle activated in adipocytes by antidiabetic agents," *Nature Medicine 8*(10):1122-1128, 2002.

Gupta et al, "Metabolic Syndrome: What are the risks for humans?" *BioScience Trends 4*(5):204-212, 2010.

(Continued)

*Primary Examiner* — Claire Kaufman
(74) *Attorney, Agent, or Firm* — Seed IP Law Group PLLC

(57) ABSTRACT

TSHR agonists that are substantially desialylated are described for treating metabolic syndrome and obesity and for inducing lipolysis. The TSHR polypeptide agonists are useful for treatment of hallmarks of metabolic syndrome: obesity, insulin resistance, hyperlipidemia, and liver steatosis, without producing a hyperthyroid state in treated individuals.

8 Claims, No Drawings

(56) References Cited

OTHER PUBLICATIONS

Haemmerle et al., "Defective Lipolysis and Altered Energy Metabolism in Mice Lacking Adipose Triglyceride Lipase," *Science 312*:733-737, 2006.
Ladenson et al., "Comparison of Administration of Recombinant Human Thyrotropin With Withdrawal of Thyroid Hormone for Radioactive Iodine Scanning in Patients With Thyroid Carcinoma," *The New England Journal of Medicine 337*:888-896, 1997.
Laugwitz et al., "The human thyrotropin receptor: A heptahelical receptor capable of stimulating members of all four G protein families," *Proc. Natl. Acad. Sci. USA 93*:116-120, 1996.
Leitolf et al., "Bioengineering of Human Thyrotropin Superactive Analogs by Site-directed "Lysine-scanning" Mutagenesis," *The Journal of Biological Chemistry 275*(35):27457-27465, 2000.
Mansell et al., "Reappraisal of the Weir equation for calculation of metabolic rate," *Am. J. Physiol. 258*:R1347-R1354, 1990.
Marcus et al., "Regulation of Lipolysis during the Neonatal Period—Importance of Thyrotropin," *J. Clin. Invest. 82*:1793-1797, 1988.
Nagayama et al., "Role of Asparagine-linked Oligosaccharides in Protein Folding, Membrane Targeting, and Thyrotropin and Autoantibody Binding of the Human Thyrotropin Receptor," *The Journal of Biological Chemistry 273*(50):33423-33428, 1998.
Nakabayashi et al., "Thyrostimulin, a heterodimer of two new human glycoprotein hormone subunits, activates the thyroid-stimulating hormone receptor," *J. Clin. Invest. 109*:1445-1452, 2002.
Okada et al., "Corticotroph Localization and Thyroid-Stimulating Hormone Receptor Binding Properties of Corticotroph-derived Glycoprotein Hormone," *Molecular Endocrinology 20*(2):414-425, express article doi:10.1210/me.2005.0270, Online Publication: Oct. 6, 2005. (44 pages).
Okada et al., "A Glycoprotein Hormone Expressed in Corticotrophs Exhibits Unique Binding Properties on Thyroid-Stimulating Hormone Receptor," *Molecular Endocrinology 20*(2):414-425, 2006.
Oliveira et al., "Investigating the Paradox of Hypothyroidism and Increased Serum Thyrotropin (TSH) Levels in Sheehan's Syndrome: Characterization of TSH Carbohydrate Content and Bioactivity," *The Journal of Clinical Endocrinology & Metabolism 86*(4):1694-1699, 2001.
Papandreou et al., "Variable Carbohydrate Structures of Circulating Thyrotropin as Studied by Lectin Affinity Chromatography in Different Clinical Conditions," *Journal of Clinical Endocrinology and Metabolism 77*(2):393-398, 1993.
Schaaf et al., "Glycosylation variants of human TSH selectivity activate signal transduction pathways," *Molecular and Cellular Endocrinology 132*:185-194, 1997.
Schauer, "Achievements and challenges of sialic acid research," *Glycoconjugate Journal 17*:485-499, 2000.
Schiffelers et al., "The effect of an increased free fatty acid concentration on thermogenesis and substrate oxidation in obese and lean men," *International Journal of Obesity 25*:33-38, 2001.
Schiffelers et al., "$\beta_1$- and $\beta_2$-Adrenoceptor-Mediated Thermogenesis and Lipid Utilization in Obese and Lean Men," *The Journal of Clinical Endocrinology & Metabolism 86*(5):2191-2199, 2001.
Szkudlinski et al., "Purification and Characterization of Recombinant Human Thyrotropin (TSH) Isoforms Produced by Chinese Hamster Ovary Cells: The Role of Sialylation and Sulfation in TSH Bioactivity," *Endocrinology 133*(4):1490-1503, 1993.
Szkudlinski et al., "Thyroid-Stimulating Hormone and Thyroid-Stimulating Hormone Receptor Structure-Function Relationships," *Physiol. Rev. 82*:473-502, 2002.
Thotakura et al., "Biological Activity and Metabolic Clearance of a Recombinant Human Thyrotropin Produced in Chinese Hamster Ovary Cells," *Endocrinology 128*(1):341-348, 1991.
Watanabe et al., "Bile acids induce energy expenditure by promoting intracellular thyroid hormone activation," *Nature 439*:484-489, 2006.
Yang et al., "Obesity increases sensitivity to endotoxin liver injury: Implications for the pathogenesis of steatohepatitis," *Proc. Natl. Acad. Sci. USA 94*:2557-2562, 1997.
International Search Report, for Application No. PCT/US2006/048820, mailed Jul. 15, 2009, 11 pages.
Supplemental European Search Report, for Application No. EP 06 84 7924, mailed Jun. 28, 2010, 5 pages.
Szkudlinski et al., "Subunit-specific functions of N-linked oligosaccharides in human thyrotropin: Role of terminal residues of $\alpha$- and $\beta$-subunit oligosaccharides in metabolic clearance and bioactivity," *Proc. Natl. Acad. Sci. USA 92*:9062-9066, 1995.
Amr et al., "Role of the Carbohydrate Moiety of Human Choriogonadotropin in Its Thyrotropic Activity," *Archives of Biochemistry and Biophysics 229*(1):170-176, Feb. 15, 1984.
Fisher et al., "Acute Release of Thyrotropin in the Newborn," *The Journal of Clinical Investigation*, 48:1670-1677, 1969.
Gabrielsson et al., "Partial Genome Scale Analysis of Gene Expression in Human Adipose Tissue Using DNA Array," *Obesity Research*, 8(5):374-384, 2000.
Gyves et al., "Alterations in the Glycosylation of Secreted Thyrotropin during Ontogenesis," *The Journal of Biological Chemistry*, 264(11):6104-6110, 1989.
Nimtz et al., "Structures of sialylated oligosaccharides of human erythropoietin expressed in recombinant BHK-21 cells," *Eur. J. Biochem. 213*:39-56, 1993.
Taylor et al., "The Paraventricular Nucleus of the Hypothalamus Has a Major Role in Thyroid Hormone Feedback Regulation of Thyrotropin Synthesis and Secretion," *Endocrinology*, 126(1):317-324, 1990.
Bundy et al., "Artichoke leaf extract (*Cynara scolymus*) reduces plasma cholesterol in otherwise healthy hypercholesterolemic adults: a randomized, double blind placebo controlled trial." *Phytomedicine 15*(9):668-675, 2008, abstract only.
Menendez et al., "TSH stimulates leptin secretion by a direct effect on adipocytes," *Journal of Endocrinology 176*:7-12, 2003.
Rodrigues et al., "Impact of cholesterol on ABC and SLC transporters expression and function and its role in disposition variability to lipid-lowering drugs." *Pharmacogenomics 10*(6):1007-1016, 2009, abstract only.
Santini et al., "Acute exogenous TSH administration stimulates leptin secretion in vivo," *Europeans Journal of Endocrinology 163*:63-67, 2010.
Sivak et al., "Protonated nanostructured aluminosilicate (NSAS) reduces plasma cholesterol concentrations and atherosclerotic lesions in Apolipoprotein E deficient mice fed a high cholesterol and high fat diet," *Lipids in Health and Disease 8*(30):doi:10.1186/1476-511X-8-30, 2009.
Utiger, Robert D., *Endocrinology and Metabolism* (Felig and Frohman, eds), pp. 261-309, 330-334 (McGraw Hill, 2001).
Braverman et al., "Recombinant Human Thyrotropin Stimulates Thyroid Function and Radioactive Iodine Uptake in the Rhesus Monkey," *J Clin Endocrinol Metab 74*:1135-1139, 1992.
Torres et al., "Effect of Various Doses of Recombinant Human Thyrotropin on the Thyroid Radioactive Iodine Uptake and Serum Levels of Thyroid Hormones and Thyroglobulin in Normal Subjects," *J Clin Endocrinol Metab 86*:1660-1664, 2001.
Benet et al., "Design and Optimization of Dosage Regimens," in Hardman et al. (eds.), *Goodman and Gilman's The Pharmacological Basis of Therapeutics*, 9th edition, New York: McGraw-Hill, 1996, p. 24.
Cole et al., "Recombinant Human Thyroid Stimulating Hormone: Development of a Biotechnology Product for Detection of Metastatic Lesions of Thyroid Carcinoma," *Bio/Technology 11*:1014-1024, Sep. 1993.
Collins et al., "Impaired Expression and Functional Activity of the $\beta_3$- and $\beta_1$-Adrenergic Receptors in Adipose Tissue of Congenitally Obese (C57BL/6J *ob/ob*) Mice," *Molecular Endocrinology 8*(4):518-527, 1994.
Farooqi et al., "Beneficial effects of leptin on obesity, T cell hyporesponsiveness, and neuroendocrine/metabolic dysfunction of human congenital leptin deficiency," *The Journal of Clinical Investigation 110*(8):1093-1103, Oct. 2002.

(56) References Cited

OTHER PUBLICATIONS

Farooqi et al., "Human disorders of leptin action," *Journal of Endocrinology 223*(1):T63-T70, 2014.
Fatourechi, "Subclinical Hypothyroidism: An Update for Primary Care Physicians," *Mayo Clin Proc. 84*(1):65-71, Jan. 2009.
Guo et al., "Leptin Signaling Targets the Thyrotropin-Releasing Hormone Gene Promoter in Vivo," *Endocrinology 145*(5):2221-2227, 2004.
Halaas et al., "Physiological response to long-term peripheral and central leptin infusion in lean and obese mice," *Proc. Natl. Acad. Sci. USA 94*:8878-8883, Aug. 1997.
Hershman et al., "Serum Thyrotropin (TSH) Levels after Thyroid Ablation Compared with TSH Levels after Exogenous Bovine TSH: Implications for $^{131}$I Treatment of Thyroid Carcinoma," *The Journal of Clinical Endocrinology and Metabolism 34*(5):814-818, May 1972.
Heymsfield et al., "Recombinant Leptin for Weight Loss in Obese and Lean Adults," *JAMA 282*(16):1568-1575, Oct. 27, 1999.
Iqbal et al., "Serum lipid levels in relation to serum thyroid-stimulating hormone and the effect of thyroxine treatment on serum lipid levels in subjects with subclinical hypothyroidism: the Tromsø Study," Abstract, *Journal of Internal Medicine 260*(1):53-61, 2006.
Kadowaki et al., "Adiponectin and adiponectin receptors in insulin resistance, diabetes, and the metabolic syndrome," *The Journal of Clinical Investigation 116*(7):1784-1792, Jul. 2006.
Klein et al., "Adipose Tissue Leptin Production and Plasma Leptin Kinetics in Humans," *Diabetes 45*:984-987, Jul. 1996.
Kleinau et al., "Novel Insights on Thyroid-Stimulating Hormone Receptor Signal Transduction," *Endocrine Reviews 34*(5):691-724, Oct. 2013.
Licinio et al., "Phenotypic effects of leptin replacement on morbid obesity, diabetes mellitus, hypogonadism, and behavior in leptin-deficient adults," *PNAS 101*(13):4531-4536, Mar. 30, 2004.
Meier et al., "Diagnostic Use of Recombinant Human Thyrotropin in Patients with Thyroid Carcinoma (Phase I/II Study)," *Journal of Clinical Endocrinology and Metabolism 78*(1):188-196, 1994.
Pelleymounter et al., "Efficacy of exogenous recombinant murine leptin in lean and obese 10- to 12-mo-old female CD-1 mice," *Am. J. Physiol. 275*(4):R950-R959, 1998.
Raisch et al., "Chapter 48: The New Drug Approval Process and Clinical Trial Design," in Troy (ed.), *Remington: The Science and Practice of Pharmacy*, 21$^{st}$ edition, Baltimore: Lippincott Williams & Wilkins, 2005, p. 965.
Rosenbaum et al., "Low-dose leptin reverses skeletal muscle, autonomic, and neuroendocrine adaptations to maintenance of reduced weight," *The Journal of Clinical Investigation 115*(12):3579-3786, Dec. 2005.
Rosenbaum et al., "Leptin reverses weight loss-induced changes in regional neural activity responses to visual food stimuli," *The Journal of Clinical Investigation 118*(7):2583-2591, 2008.
Schaaf et al., "Thyrotropin-releasing hormone time-dependently influences thyrotropin microheterogeneity—an in vivo study in euthyroidism," *Journal of Endocrinology 166*:137-143, 2000.
Snitker et al., "Whole body fat oxidation is related to in situ adipose tissue lipolytic response to isoproterenol in males," *Am. J. Physiol. 275*(3):E400-E404, 1998.
ThyCa: Thyroid Cancer Survivors' Association, Inc., "Low-Iodine Diet Guidelines—1-Page Summary," *Low Iodine Cookbook*, 8$^{th}$ edition, 2015, retrieved from www.thyca.org, 1 page.
Tian et al., "A Novel Role for Thyroid-Stimulating Hormone: Up-Regulation of Hepatic 3-Hydroxy-3-Methyl-Glutaryl-Coenzyme A Reductase Expression Through the Cyclic Adenosine Monophosphate/Protein Kinase A/Cyclic Adenosine Monophosphate-Responsive Element Binding Protein Pathway," *Hepatology 52*(4):1401-1409, Oct. 2010.
U.S. Department of Health and Human Services, "Guidance for Industry: Estimating the Maximum Safe Starting Dose in Initial Clinical Trials for Therapeutics in Adult Healthy Volunteers," Jul. 2005, 30 pages.
Zhang et al., "Presence of thyrotropin receptor in hepatocytes: not a case of illegitimate transcription," *J. Cell. Mol. Med. 13*(11-12):4636-4642, 2009.

* cited by examiner

```
                         SEQUENCE LISTING


<160> NUMBER OF SEQ ID NOS: 16

<210> SEQ ID NO 1
<211> LENGTH: 116
<212> TYPE: PRT
<213> ORGANISM: Homo sapiens

<400> SEQUENCE: 1

Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115


<210> SEQ ID NO 2
<211> LENGTH: 138
<212> TYPE: PRT
<213> ORGANISM: Homo sapiens

<400> SEQUENCE: 2

Met Thr Ala Leu Phe Leu Met Ser Met Leu Phe Gly Leu Ala Cys Gly
 1               5                  10                  15

Gln Ala Met Ser Phe Cys Ile Pro Thr Glu Tyr Thr Met His Ile Glu
            20                  25                  30

Arg Arg Glu Cys Ala Tyr Cys Leu Thr Ile Asn Thr Thr Ile Cys Ala
        35                  40                  45

Gly Tyr Cys Met Thr Arg Asp Ile Asn Gly Lys Leu Phe Leu Pro Lys
    50                  55                  60

Tyr Ala Leu Ser Gln Asp Val Cys Thr Tyr Arg Asp Phe Ile Tyr Arg
65                  70                  75                  80

Thr Val Glu Ile Pro Gly Cys Pro Leu His Val Ala Pro Tyr Phe Ser
                85                  90                  95
```

```
Tyr Pro Val Ala Leu Ser Cys Lys Cys Gly Lys Cys Asn Thr Asp Tyr
            100                 105                 110

Ser Asp Cys Ile His Glu Ala Ile Lys Thr Asn Tyr Cys Thr Lys Pro
        115                 120                 125

Gln Lys Ser Tyr Leu Val Gly Phe Ser Val
    130                 135


<210> SEQ ID NO 3
<211> LENGTH: 129
<212> TYPE: PRT
<213> ORGANISM: Homo sapiens

<400> SEQUENCE: 3

Met Pro Met Ala Ser Pro Gln Thr Leu Val Leu Tyr Leu Leu Val Leu
 1               5                  10                  15

Ala Val Thr Glu Ala Trp Gly Gln Glu Ala Val Ile Pro Gly Cys His
            20                  25                  30

Leu His Pro Phe Asn Val Thr Val Arg Ser Asp Arg Gln Gly Thr Cys
        35                  40                  45

Gln Gly Ser His Val Ala Gln Ala Cys Val Gly His Cys Glu Ser Ser
    50                  55                  60

Ala Phe Pro Ser Arg Tyr Ser Val Leu Val Ala Ser Gly Tyr Arg His
65                  70                  75                  80

Asn Ile Thr Ser Val Ser Gln Cys Cys Thr Ile Ser Gly Leu Lys Lys
                85                  90                  95

Val Lys Val Gln Leu Gln Cys Val Gly Ser Arg Arg Glu Glu Leu Glu
            100                 105                 110

Ile Phe Thr Ala Arg Ala Cys Gln Cys Asp Met Cys Arg Leu Ser Arg
        115                 120                 125

Tyr


<210> SEQ ID NO 4
<211> LENGTH: 130
<212> TYPE: PRT
<213> ORGANISM: Homo sapiens

<400> SEQUENCE: 4

Met Lys Leu Ala Phe Leu Phe Leu Gly Pro Met Ala Leu Leu Leu Leu
 1               5                  10                  15

Ala Gly Tyr Gly Cys Val Leu Gly Ala Ser Ser Gly Asn Leu Arg Thr
            20                  25                  30

Phe Val Gly Cys Ala Val Arg Glu Phe Thr Phe Leu Ala Lys Lys Pro
        35                  40                  45

Gly Cys Arg Gly Leu Arg Ile Thr Thr Asp Ala Cys Trp Gly Arg Cys
    50                  55                  60

Glu Thr Trp Glu Lys Pro Ile Leu Glu Pro Pro Tyr Ile Glu Ala His
65                  70                  75                  80

His Arg Val Cys Thr Tyr Asn Glu Thr Lys Gln Val Thr Val Lys Leu
                85                  90                  95

Pro Asn Cys Ala Pro Gly Val Asp Pro Phe Tyr Thr Tyr Pro Val Ala
            100                 105                 110

Ile Arg Cys Asp Cys Gly Ala Cys Ser Thr Ala Thr Thr Glu Cys Glu
        115                 120                 125

Thr Ile
    130
```

```
<210> SEQ ID NO 5
<211> LENGTH: 24
<212> TYPE: PRT
<213> ORGANISM: Homo sapiens

<400> SEQUENCE: 5

Met Asp Tyr Tyr Arg Lys Tyr Ala Ala Ile Phe Leu Val Thr Leu Ser
 1               5                  10                  15

Val Phe Leu His Val Leu His Ser
            20


<210> SEQ ID NO 6
<211> LENGTH: 92
<212> TYPE: PRT
<213> ORGANISM: Homo sapiens

<400> SEQUENCE: 6

Ala Pro Asp Val Gln Asp Cys Pro Glu Cys Thr Leu Gln Glu Asn Pro
 1               5                  10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90


<210> SEQ ID NO 7
<211> LENGTH: 20
<212> TYPE: PRT
<213> ORGANISM: Homo sapiens

<400> SEQUENCE: 7

Met Thr Ala Leu Phe Leu Met Ser Met Leu Phe Gly Leu Ala Cys Gly
 1               5                  10                  15

Gln Ala Met Ser
            20


<210> SEQ ID NO 8
<211> LENGTH: 118
<212> TYPE: PRT
<213> ORGANISM: Homo sapiens

<400> SEQUENCE: 8

Phe Cys Ile Pro Thr Glu Tyr Thr Met His Ile Glu Arg Arg Glu Cys
 1               5                  10                  15

Ala Tyr Cys Leu Thr Ile Asn Thr Thr Ile Cys Ala Gly Tyr Cys Met
            20                  25                  30

Thr Arg Asp Ile Asn Gly Lys Leu Phe Leu Pro Lys Tyr Ala Leu Ser
        35                  40                  45

Gln Asp Val Cys Thr Tyr Arg Asp Phe Ile Tyr Arg Thr Val Glu Ile
    50                  55                  60

Pro Gly Cys Pro Leu His Val Ala Pro Tyr Phe Ser Tyr Pro Val Ala
65                  70                  75                  80

Leu Ser Cys Lys Cys Gly Lys Cys Asn Thr Asp Tyr Ser Asp Cys Ile
                85                  90                  95
```

```
His Glu Ala Ile Lys Thr Asn Tyr Cys Thr Lys Pro Gln Lys Ser Tyr
            100                 105                 110

Leu Val Gly Phe Ser Val
        115


<210> SEQ ID NO 9
<211> LENGTH: 23
<212> TYPE: PRT
<213> ORGANISM: Homo sapiens

<400> SEQUENCE: 9

Met Pro Met Ala Ser Pro Gln Thr Leu Val Leu Tyr Leu Leu Val Leu
 1               5                  10                  15

Ala Val Thr Glu Ala Trp Gly
            20


<210> SEQ ID NO 10
<211> LENGTH: 106
<212> TYPE: PRT
<213> ORGANISM: Homo sapiens

<400> SEQUENCE: 10

Gln Glu Ala Val Ile Pro Gly Cys His Leu His Pro Phe Asn Val Thr
 1               5                  10                  15

Val Arg Ser Asp Arg Gln Gly Thr Cys Gln Gly Ser His Val Ala Gln
            20                  25                  30

Ala Cys Val Gly His Cys Glu Ser Ser Ala Phe Pro Ser Arg Tyr Ser
        35                  40                  45

Val Leu Val Ala Ser Gly Tyr Arg His Asn Ile Thr Ser Val Ser Gln
    50                  55                  60

Cys Cys Thr Ile Ser Gly Leu Lys Lys Val Lys Val Gln Leu Gln Cys
65                  70                  75                  80

Val Gly Ser Arg Arg Glu Glu Leu Glu Ile Phe Thr Ala Arg Ala Cys
                85                  90                  95

Gln Cys Asp Met Cys Arg Leu Ser Arg Tyr
            100                 105


<210> SEQ ID NO 11
<211> LENGTH: 24
<212> TYPE: PRT
<213> ORGANISM: Homo sapiens

<400> SEQUENCE: 11

Met Lys Leu Ala Phe Leu Phe Leu Gly Pro Met Ala Leu Leu Leu Leu
 1               5                  10                  15

Ala Gly Tyr Gly Cys Val Leu Gly
            20


<210> SEQ ID NO 12
<211> LENGTH: 106
<212> TYPE: PRT
<213> ORGANISM: Homo sapiens

<400> SEQUENCE: 12

Ala Ser Ser Gly Asn Leu Arg Thr Phe Val Gly Cys Ala Val Arg Glu
 1               5                  10                  15

Phe Thr Phe Leu Ala Lys Lys Pro Gly Cys Arg Gly Leu Arg Ile Thr
            20                  25                  30

Thr Asp Ala Cys Trp Gly Arg Cys Glu Thr Trp Glu Lys Pro Ile Leu
        35                  40                  45
```

```
Glu Pro Pro Tyr Ile Glu Ala His His Arg Val Cys Thr Tyr Asn Glu
    50                  55                  60

Thr Lys Gln Val Thr Val Lys Leu Pro Asn Cys Ala Pro Gly Val Asp
65                  70                  75                  80

Pro Phe Tyr Thr Tyr Pro Val Ala Ile Arg Cys Asp Cys Gly Ala Cys
                85                  90                  95

Ser Thr Ala Thr Thr Glu Cys Glu Thr Ile
            100                 105


<210> SEQ ID NO 13
<211> LENGTH: 351
<212> TYPE: DNA
<213> ORGANISM: Homo sapiens

<400> SEQUENCE: 13

atggattact acagaaaata tgcagctatc tttctggtca cattgtcggt gtttctgcat     60

gttctccatt ccgctcctga tgtgcaggat tgcccagaat gcacgctaca ggaaaaccca    120

ttcttctccc agccgggtgc cccaatactt cagtgcatgg gctgctgctt ctctagagca    180

tatcccactc cactaaggtc caagaagacg atgttggtcc aaaagaacgt cacctcagag    240

tccacttgct gtgtagctaa atcatataac agggtcacag taatgggggg tttcaaagtg    300

gagaaccaca cggcgtgcca ctgcagtact tgttattatc acaaatctta a             351


<210> SEQ ID NO 14
<211> LENGTH: 417
<212> TYPE: DNA
<213> ORGANISM: Homo sapiens

<400> SEQUENCE: 14

atgactgctc tctttctgat gtccatgctt tttggccttg catgtgggca agcgatgtct     60

ttttgtattc caactgagta tacaatgcac atcgaaagga gagagtgtgc ttattgccta    120

accatcaaca ccaccatctg tgctggatat tgtatgacac gggatatcaa tggcaaactg    180

tttcttccca aatatgctct gtcccaggat gtttgcacat atagagactt catctacagg    240

actgtagaaa taccaggatg cccactccat gttgctccct atttttccta tcctgttgct    300

ttaagctgta agtgtggcaa gtgcaatact gactatagtg actgcataca tgaagccatc    360

aagacaaact actgtaccaa acctcagaag tcttatctgg taggattttc tgtctaa       417


<210> SEQ ID NO 15
<211> LENGTH: 746
<212> TYPE: DNA
<213> ORGANISM: Homo sapiens

<400> SEQUENCE: 15

ccagcaggag gcacaggaaa actgcaagcc gctctgttcc tgggcctcgg aagtgatgcc     60

tatggcgtcc cctcaaaccc tggtcctcta tctgctggtc ctggcagtca ctgaagcctg    120

gggccaggag gcagtcatcc caggctgcca cttgcacccc ttcaatgtga cagtgcgaag    180

tgaccgccaa ggcacctgcc agggctccca cgtggcacag gcctgtgtgg gccactgtga    240

gtccagcgcc ttcccttctc ggtactctgt gctggtggcc agtggttacc gacacaacat    300

cacctccgtc tctcagtgct gcaccatcag tggcctgaag aaggtcaaag tacagctgca    360

gtgtgtgggg agccggaggg aggagctcga gatcttcacg gccagggcct gccagtgtga    420

catgtgtcgc ctctctcgct actagcccat cctctcccct ccttcctccc ctgggtcaca    480

gggcttgaca ttctggtggg ggaaacctgt gttcaagatt caaaaactgg aaggagctcc    540
```

-continued

```
agccctgatg gttacttgct atggaatttt tttaaataag gggagggttg ttccagcttt    600

gatcctttgt aagattttgt gactgtcacc tgagaagagg ggagtttctg cttcttccct    660

gcctctgcct ggcccttcta aaccaatctt tcatcatttt acttccctct ttgcccttac    720

ccctaaataa agcaagcagt tcttga                                         746


<210> SEQ ID NO 16
<211> LENGTH: 390
<212> TYPE: DNA
<213> ORGANISM: Homo sapiens

<400> SEQUENCE: 16

atgaagctgg cattcctctt ccttggcccc atggccctcc tccttctggc tggctatggc     60

tgtgtcctcg gtgcctccag tgggaacctg cgcacctttg tgggctgtgc cgtgagggag    120

tttactttcc tggccaagaa gccaggctgc aggggccttc ggatcaccac ggatgcctgc    180

tggggtcgct gtgagacctg ggagaaaccc attctggaac ccccctatat tgaagcccat    240

catcgagtct gtacctacaa cgagaccaaa caggtgactg tcaagctgcc caactgtgcc    300

ccgggagtcg acccccttcta cacctatccc gtggccatcc gctgtgactg cggagcctgc    360

tccactgcca ccacggagtg tgagaccatc                                     390
```

THYROID-STIMULATING HORMONE RECEPTOR POLYPEPTIDE AGONIST GLYCOFORMS TO TREAT METABOLIC SYNDROME

CROSS-REFERENCE TO RELATED APPLICATIONS

This application is a continuation application of U.S. application Ser. No. 12/158,796, having a filing date of Dec. 3, 2008, which is a national stage application filed under 35 U.S.C. §371 of International Application No. PCT/US2006/048820, accorded an international filing date of Dec. 21, 2006, which claims the benefit of U.S. Provisional Patent Application No. 60/753,798 filed Dec. 23, 2005, all of which applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 620042_401C1_SEQUENCE_LISTING.txt. The text file is 16 KB, was created on Feb. 17, 2010, and is being submitted electronically via EFS-Web.

BACKGROUND OF THE INVENTION

1. Field of the Invention

The present invention relates to improved methods for the treatment of metabolic syndrome, which includes diabetes, cardiovascular disease, hyperlipidemia, liver steatosis, and obesity. More particularly, provided herein are glycosylation isoforms of TSH receptor (TSHR) agonists that exhibit increased bioactivity on adipose tissue for treatment of metabolic syndrome, and yet avoid thyrotoxicosis, the chronic hyperthyroid state.

2. Description of the Related Art

Metabolic syndrome is a public health problem that is both serious and widespread. Metabolic syndrome in humans is typically associated with obesity and characterized by one or more of the following: cardiovascular disease, liver steatosis, hyperlipidemia, diabetes, and insulin resistance. One third of the population in industrialized countries has an excess weight of at least 20% relative to the ideal weight. This phenomenon has spread to the developing world, particularly to the regions of the globe where economies are modernizing. As of the year 2000, there were an estimated 300 million obese people worldwide. Obesity is frequently attributed to consumption of a high fat diet, inactivity, and genetic predisposition.

Obesity considerably increases the risk of developing cardiovascular or metabolic diseases. For an excess weight greater than 30%, the incidence of coronary disease is doubled in subjects less than 50 years of age. Studies carried out for other diseases are equally revealing. For an excess weight of 20%, the risk of high blood pressure is doubled. For an excess weight of 30%, the risk of developing non-insulin dependent diabetes is tripled, and the incidence of dyslipidemia increases six fold. The list of additional diseases promoted by obesity is long; abnormalities in hepatic function, digestive pathologies, certain cancers, and psychological disorders are prominent among them.

Treatments for obesity include restriction of caloric intake and increased caloric expenditure through physical exercise. However, the treatment of obesity by dieting, although effective in the short-term, suffers from an extremely high rate of recidivism. Treatment with exercise has been shown to be relatively ineffective when applied in the absence of dieting. Other treatments include gastrointestinal surgery or agents that limit the absorption of dietary lipids. These strategies have been largely unsuccessful due to side effects of their use. Current therapies for complications associated with obesity, including type-2 diabetes, hyperlipidemia, and steatohepatitis, have been inadequate to halt the progression of these life-threatening pathologies in most instances.

Lipolysis is the biochemical process by which stored fats in the form of triglycerides are released from fat cells as individual free fatty acids (FFA) into the circulation. Stimulation of lipolysis has been clearly linked to increased energy expenditure in humans, and several strategies to promote lipolysis and increase oxidation of lipids have been investigated to promote weight loss and treat aspects of metabolic syndrome associated with obesity. These therapeutic efforts primarily focus on creating compounds that stimulate the sympathetic nervous system (SNS) through its peripheral β-adrenoreceptors.

Lipolytic agents have been investigated extensively in rodents, dogs, and primates and found to produce striking improvements in adiposity, glucose sensitivity, and dyslipidemia, hallmarks of the metabolic syndrome. These agents, agonists of sympathetic nervous system catecholamines, have not proven to be successful therapeutics in humans principally due to the inability thus far to create specific agents that target only adipose tissue without stimulating other tissues responsive to sympathetic innervation.

Energy expenditure represents one side of the energy balance equation. In order to maintain stable weight, energy expenditure should be in equilibrium with energy intake. Considerable efforts have been made to manipulate energy intake (i.e., diet and appetite) as a means of maintaining or losing weight; however, despite enormous sums of money devoted to these approaches, they have been largely unsuccessful. There have also been efforts to increase energy expenditure pharmacologically as a means of managing weight control and treating obesity. Increasing metabolic rate is an attractive therapeutic approach because it has the potential of allowing affected individuals to maintain food intake at normal levels. Further evidence supports the view that increases in energy expenditure due to pharmacological means are not fully counteracted by corresponding increases in energy intake and appetite. See Bray, G. A. (1991) *Ann Rev Med* 42, 205-216.

Much of the energy expended on a daily basis derives from resting metabolic rate (RMR), which comprises 50-80% of the total daily energy expenditure. For a review, see Astrup, A. (2000) *Endocrine* 13, 207-212. Noradrenaline turnover studies have shown that most of the variability in RMR that is unexplained by body size and composition is related to differences in SNS activity, suggesting that SNS activity does modulate RMR. See Snitker, S., et al. (2001) *Obes. Rev.* 1:5-15. Meal ingestion is accompanied by increased SNS activity, and studies have demonstrated that increased SNS activity in response to a meal accounts for at least part of meal-induced thermogenesis.

The peripheral targets of the SNS involved in the regulation of energy utilization are the β-adrenoreceptors (β-AR's). These receptors are coupled to the second messenger cyclic adenosine monophosphate (cAMP). Elevation of cAMP levels leads to activation of protein kinase A (PKA), a multipotent protein kinase and transcription factor eliciting diverse cellular effects. See Bourne, H. R., et al. (1991) *Nature* 349: 117-127. Adipose tissue is highly innervated by the SNS, and possesses three known subtypes of β-adrenoreceptors, $\beta_1$-, $\beta_2$-, and $\beta_3$-AR. Activation of the SNS stimulates energy expenditure via coupling of these receptors to lipolysis and fat oxidation. Increased serum free fatty acids (FFAs) produced by adipose tissue and released into the bloodstream stimulate energy expenditure and increase thermogenesis. For a review, see Astrup, A. (2000) *Endocrine* 13, 207-212. In addition, elevated PKA levels increase energy utilization in fat by up-regulating uncoupling protein-1 (UCP-1), which creates a futile cycle in mitochondria, generating waste heat.

Over the past two decades, investigation of the physiological benefits of SNS activation for the treatment of obesity and treatment of diabetes related to obesity has centered on pharmacological activation of the $\beta_3$-AR. Expression of the $\beta_3$-AR is restricted to a narrower range of tissues than the $\beta_1$ or $\beta_2$ isoforms, and is highly expressed in rodent adipose tissue compared to the other isoforms. Experimental work in rodents treated with $\beta_3$-AR agonists has demonstrated that stimulation of lipolysis and fat oxidation produces increased energy expenditure, weight loss, and increased insulin sensitivity. See de Souza, C. J. and Burkey, B. F. (2001) *Curr. Pharm. Des.* 7, 1433-1449. However, the potential benefits of the $\beta_3$-AR agonists have not been realized, due to their lack of efficacy at the human $\beta_3$-AR. Further, it has more recently been shown that the levels of $\beta_3$-AR in rodent adipose tissue are much higher than in human adipose tissue. In human adipose tissue, the $\beta_1$ and $\beta_2$ isoforms represent the predominant adrenoreceptor isoforms. See Arch, J. R. (2002) *Eur. J. Pharmacol.* 440:99-107. Thus, although stimulation of lipolysis has been demonstrated in rodents, the mechanism for therapeutically producing the corresponding effects in humans is unrealized.

Energy expenditure can be stimulated pharmacologically by manipulation of the central nervous system, by activation of the peripheral efferents of the SNS, or by increasing thyroid hormone levels. Thyroid hormone stimulates carbohydrate and lipid catabolism in most cells of the body and increases the rate of protein synthesis. Thyroid-stimulating hormone (TSH) stimulates thyroid hormone biosynthesis and secretion. The secretion of TSH from the thyrotrophs of the anterior pituitary is inhibited by circulating $T_4$ and $T_3$ and stimulated by thyrotropin-releasing hormone (TRH) produced in the hypothalamus. See Utiger, in. *Endocrinology and Metabolism* (Felig and Frohman, eds), pp. 261-347, McGraw-Hill, (2001). The hypothalamic-pituitary-thyroid (HPT) axis is a classical endocrine feedback pathway negatively regulated by thyroid hormone $T_3$, which is released by the thyroid gland or synthesized in tissues from $T_4$, the other form of thyroid hormone released by the thyroid gland. Release of hypothalamic TRH is inhibited by $T_3$, and synthesis of pituitary TSH is inhibited by $T_3$.

As a result of the catabolism produced by thyroid hormone, heat is given off and energy expenditure is increased. There has been an intense interest in thyroid hormone levels in obesity, due to the opportunity to increase basal energy consumption by increasing thyroid hormone levels. Studies of thyroid tissue have revealed that the thyroid receives persistent stimulation with TSH. The thyroid is a slow-reacting organ, with thyrocytes requiring sustained 18-hour TSH stimulation in order to initiate DNA synthesis and proliferation. See Roger, P. et al. (1987) *J. Cell Physiol.* 130, 58-67.

Recombinant human TSH (rhTSH) has been introduced into humans (Thyrogen®, Genzyme Corporation, Cambridge, Mass.) and has a much lower metabolic clearance rate (MCR) than human pituitary-derived TSH. Estimates of the mean apparent elimination half-life are 25+/−10 hours. Serum concentrations of rhTSH are significantly elevated up to 24 hours after a single injection of approximately 30 μg/kg in human subjects. See Ladenson, P. W. et al. (1997) *N. Engl. J. Med.* 337, 888-896. Human pituitary TSH is a glycoprotein mixture of oligosaccharide isoforms, including sulfated oligosaccharides, sialylated oligosaccharides, and oligosaccharides that lack anionic groups. In the hypothyroid state, sustained exposure to TSH is needed to increase thyroid hormone release and sialylated TSH produces greater in vivo thyroid-stimulating activity than other TSH glycoforms.

However, studies have revealed that obese and normal-weight individuals have similar thyroid hormone profiles. An excess of thyroid hormone leads to various disorders, generally termed thyrotoxicosis. This condition is characterized by an abnormally high metabolic rate, increased blood pressure, high body temperature, heat intolerance, irritability, and tremors of the fingers. Of particular concern in the obese state is the tendency toward increased and more forceful heartbeats. Due to the adverse effects of elevated thyroid hormone levels, the use of thyroid hormone to treat obesity has seen little success, other than in the small fraction of obese patients identified with hypothyroidism.

Clearly a need remains for improved treatments that are useful for stimulating lipolysis and treating metabolic syndrome without producing potentially serious side effects associated with the hyperthyroid state. The present invention fulfills such needs and offers other related advantages.

BRIEF SUMMARY OF THE INVENTION

The present invention in one embodiment provides a method of treating metabolic syndrome in a subject, comprising administering to the subject, under conditions and for a time sufficient to induce lipolysis in one or a plurality of adipocytes without inducing thyrotoxicosis in the subject, a composition that comprises an autologous thyroid-stimulating hormone receptor (TSHR) agonist and a pharmaceutically acceptable carrier, wherein said TSHR agonist is substantially desialylated. In one embodiment, the TSHR agonist comprises at least one glycoprotein having at least one N-linked oligosaccharide moiety that is substantially desialylated. In a specific embodiment, the TSHR agonist comprises a glycoprotein preparation that comprises one or a plurality of glycoprotein molecules each of which has at least one N-linked oligosaccharide moiety, wherein the TSHR agonist is selected from a glycoprotein preparation that is at least 85% desialylated, a glycoprotein preparation that is at least 90% desialylated, a glycoprotein preparation that is at least 95% desialylated, and a glycoprotein preparation that is at least 98% desialylated. In another specific embodiment, the TSHR agonist comprises a glycoprotein preparation that comprises one or a plurality of glycoprotein molecules each of which has at least two N-linked oligosaccharide moieties, wherein the TSHR agonist is selected from a glycoprotein preparation that is at least 85% desialylated, a glycoprotein preparation that is at least 90% desialylated, a glycoprotein preparation that is at least 95% desialylated, and a glycoprotein preparation that is at least 98% desialylated. In yet another specific embodiment, the TSHR agonist comprises a glycoprotein preparation that comprises one or a plurality of glycoprotein molecules each of which has at least three N-linked oligosaccharide moieties, wherein the TSHR agonist is selected from a glycoprotein preparation that is at least 85% desialylated, a glycoprotein preparation that is at least 90% desialylated, a glycoprotein preparation that is at least 95% desialylated and a glycoprotein preparation that is at least 98% desialylated. In a certain embodiment, the TSHR agonist comprises a glycoprotein preparation that lacks detectable sialic acid. In a certain specific embodiment, the TSHR agonist that is substantially desialylated is selected from a substantially desialylated thyroid-stimulating hormone (TSH) and a substantially desialylated corticotroph-derived glycoprotein hormone (CGH). In another particular embodiment, the TSHR agonist comprises a thyroid-stimulating hormone (TSH) glycoprotein preparation that is selected from a TSH glycoprotein preparation that is at least 85% desialylated, a TSH glycoprotein preparation that is at least 90% desialylated, a TSH glycoprotein preparation that is at least 95% desialylated and a TSH glycoprotein preparation that is at least 98% desialylated. In still another specific embodiment, the TSHR agonist comprises a corticotroph-derived glycoprotein hormone (CGH) glycoprotein preparation that is selected from a CGH glycoprotein preparation that is at least 85% desialylated, a CGH glycoprotein preparation that is at least 90% desialylated, a CGH glycoprotein preparation that is at least 95% desialylated and a CGH glycoprotein preparation that is at least 98% desialylated. In one embodiment, the TSHR agonist comprises a glycoprotein preparation that is selected from a thyroid-stimulating hormone (TSH) glycoprotein preparation that lacks detectable sialic acid and a corticotroph-derived glycoprotein hormone (CGH) glycoprotein preparation that lacks detectable sialic acid. In another specific embodiment, the subject is a human and the TSHR agonist is a human TSHR agonist, which is a substantially desialylated human TSHR agonist as described above and throughout the disclosure. In a specific embodiment, the human TSHR agonist is human TSH or human CGH. In a particular embodiment, metabolic syndrome comprises at least one metabolic disorder that is selected from the group consisting of obesity, type 2 diabetes mellitus, hyperlipidemia, insulin resistance, steatohepatitis, hypertension, dyslipidemia and atherosclerosis. In a specific embodiment, the subject (a) is obese; (b) has type 2 diabetes mellitus; or (c) is obese and has type 2 diabetes mellitus.

Also provided herein are pharmaceutical compositions comprising a TSHR agonist. In one embodiment, pharmaceutical composition is provided for treating a metabolic disorder, which composition comprises a thyroid-stimulating hormone receptor (TSHR) agonist that is substantially desialylated and a pharmaceutically acceptable carrier. In a certain embodiment, the TSHR agonist comprises at least one glycoprotein having at least one N-linked oligosaccharide moiety that is substantially desialylated. In another embodiment, the TSHR agonist comprises a glycoprotein preparation that comprises one or a plurality of glycoprotein molecules each of which has at least one N-linked oligosaccharide moiety, wherein the TSHR agonist is selected from a glycoprotein preparation that is at least 85% desialylated, a glycoprotein preparation that is at least 90% desialylated, a glycoprotein preparation that is at least 95% desialylated and a glycoprotein preparation that is at least 98% desialylated. In yet another embodiment, the TSHR agonist comprises a glycoprotein preparation that comprises one or a plurality of glycoprotein molecules each of which has at least two N-linked oligosaccharide moieties, wherein the TSHR agonist is selected from a glycoprotein preparation that is at least 85% desialylated, a glycoprotein preparation that is at least 90% desialylated, a glycoprotein preparation that is at least 95% desialylated and a glycoprotein preparation that is at least 98% desialylated. In still yet another embodiment, the TSHR agonist comprises a glycoprotein preparation that comprises one or a plurality of glycoprotein molecules each of which has at least three N-linked oligosaccharide moieties, wherein the TSHR agonist is selected from a glycoprotein preparation that is at least 85% desialylated, a glycoprotein preparation that is at least 90% desialylated, a glycoprotein preparation that is at least 95% desialylated and a glycoprotein preparation that is at least 98% desialylated. In another particular embodiment, the TSHR agonist comprises a thyroid-stimulating hormone (TSH) glycoprotein preparation that is selected from a TSH glycoprotein preparation that is at least 85% desialylated, a TSH glycoprotein preparation that is at least 90% desialylated, a TSH glycoprotein preparation that is at least 95% desialylated and a TSH glycoprotein preparation that is at least 98% desialylated. In another specific embodiment, the TSHR agonist comprises a corticotroph-derived glycoprotein hormone (CGH) glycoprotein preparation that is selected from a CGH glycoprotein preparation that is at least 85% desialylated, a CGH glycoprotein preparation that is at least 90% desialylated, a CGH glycoprotein preparation that is at least 95% desialylated and a CGH glycoprotein preparation that is at least 98% desialylated. In yet another certain embodiment, the TSHR agonist comprises a glycoprotein preparation that is selected from a thyroid-stimulating hormone (TSH) glycoprotein preparation that lacks detectable sialic acid and a corticotroph-derived glycoprotein hormone (CGH) glycoprotein preparation that lacks detectable sialic acid. In certain specific embodiments, the substantially desialylated TSHR agonist in any of the aforementioned pharmaceutical compositions is a human TSHR agonist that is substantially desialylated as described in the embodiments above and throughout the disclosure. In another specific embodiment, the substantially desialylated human TSHR agonist comprises human CGH that is substantially desialylated as described in the embodiments above and throughout the disclosure.

Also provided herein is a method of altering a metabolic activity in a subject, comprising administering to the subject, under conditions and for a time sufficient to alter at least one metabolic activity without inducing thyrotoxicosis in the subject, a composition that comprises an autologous thyroid-stimulating hormone receptor (TSHR) agonist and a pharmaceutically acceptable carrier, wherein said TSHR agonist is substantially desialylated. In a certain embodiment, altering the at least one metabolic activity comprises inducing lipolysis in at least one cell in the subject. In another certain embodiment, altering the at least one metabolic activity comprises decreasing a level of serum triglyceride in the subject. In a particular embodiment, altering the at least one metabolic activity comprises increasing metabolic rate in the subject. In yet another particular embodiment, altering the at least one metabolic activity comprises decreasing a level of blood glucose. In still another embodiment, altering the at least one metabolic activity comprises decreasing a level of plasma cholesterol. In another particular embodiment, the TSHR agonist used in the aforementioned methods comprises at least one glycoprotein having at least one N-linked oligosaccharide moiety that is substantially desialylated. In a specific embodiment, the TSHR agonist comprises a glycoprotein preparation that comprises one or a plurality of glycoprotein molecules each of which has at least one N-linked oligosaccharide moiety, wherein the TSHR agonist is selected from a glycoprotein preparation that is at least 85% desialylated, a glycoprotein preparation that is at least 90% desialylated, a glycoprotein preparation that is at least 95% desialylated and a glycoprotein preparation that is at least 98% desialylated. In another specific embodiment, the TSHR agonist comprises a glycoprotein preparation that comprises one or a plurality of glycoprotein molecules each of which has at least two N-linked oligosaccharide moieties, wherein the TSHR agonist is selected from a glycoprotein preparation that is at least 85% desialylated, a glycoprotein preparation that is at least 90% desialylated, a glycoprotein preparation that is at least 95% desialylated and a glycoprotein preparation that is at least 98% desialylated. In yet another specific embodiment, the TSHR agonist comprises a glycoprotein preparation that comprises one or a plurality of glycoprotein molecules each of which has at least three N-linked oligosaccharide moieties, wherein the TSHR agonist is selected from a glycoprotein preparation that is at least 85% desialylated, a glycoprotein preparation that is at least 90% desialylated, a glycoprotein preparation that is at least 95% desialylated and a glycoprotein preparation that is at least 98% desialylated. In a specific embodiment of the aforementioned methods, the TSHR agonist comprises a glycoprotein preparation that lacks detectable sialic acid. In another specific embodiment, the TSHR agonist that is substantially desialylated is selected from a substantially desialylated thyroid-stimulating hormone (TSH) and a substantially desialylated corticotroph-derived glycoprotein hormone (CGH). In another embodiment, the TSHR agonist comprises a thyroid-stimulating hormone (TSH) glycoprotein preparation that is selected from a TSH glycoprotein preparation that is at least 85% desialylated, a TSH glycoprotein preparation that is at least 90% desialylated, a TSH glycoprotein preparation that is at least 95% desialylated and a TSH glycoprotein preparation that is at least 98% desialylated. In still another specific embodiment, the TSHR agonist comprises a corticotroph-derived glycoprotein hormone (CGH) glycoprotein preparation that is selected from a CGH glycoprotein preparation that is at least 85% desialylated, a CGH glycoprotein preparation that is at least 90% desialylated, a CGH glycoprotein preparation that is at least 95% desialylated and a CGH glycoprotein preparation that is at least 98% desialylated. In another particular embodiment, the TSHR agonist comprises a glycoprotein preparation that is selected from the group consisting of a thyroid-stimulating hormone (TSH) glycoprotein preparation that lacks detectable sialic acid and a corticotroph-derived glycoprotein hormone (CGH) glycoprotein preparation that lacks detectable sialic acid. In a particular embodiment, the subject is a human and the TSHR agonist is a human TSHR agonist. In a specific embodiment, the human TSHR agonist comprises human TSH that is substantially desialylated, as described in the embodiments above and throughout the disclosure. In another specific embodiment, the human TSHR agonist comprises human CGH that is substantially desialylated as described in the embodiments above and throughout the disclosure.

In other embodiments, a use is provided for any one of the substantially desialylated TSHR agonists described herein for the manufacture of a medicament for treating metabolic syndrome, which may include at least one metabolic disorder that is selected from obesity, type 2 diabetes mellitus, hyperlipidemia, insulin resistance, steatohepatitis, hypertension, dyslipidemia and atherosclerosis. In certain other embodiments, a use is provided for any one of the substantially desialylated TSHR agonists described herein for the manufacture of a medicament for altering at least one metabolic activity without inducing thyrotoxicosis in the subject, wherein altering the at least one metabolic activity comprises any one or more of inducing lipolysis in at least one cell in the subject; decreasing a level of serum triglyceride in the subject; increasing metabolic rate in the subject; decreasing a level of blood glucose; and decreasing a level of plasma cholesterol.

These and other embodiments of the present invention will become apparent upon reference to the following detailed description. All U.S. patents, U.S. patent application publications, U.S. patent applications, foreign patents, foreign patent applications and non-patent publications referred to in this specification and/or listed in the Application Data Sheet, are incorporated herein by reference, each in their entirety.

DETAILED DESCRIPTION OF THE INVENTION

The present invention relates generally to improved methods for stimulating lipolysis in adipose cells and/or tissue. As described in detail herein, thyroid-stimulating hormone receptor (TSHR) agonists, such as substantially desialylated glycoforms, can be used to produce a potent lipolytic stimulus, with related therapeutic benefits of SNS innervation of adipose tissue, without induction or maintenance of a chronic hyperthyroid state in treated subjects. The TSHR agonists described herein have increased bioactivity and shorter circulatory half-life than other TSHR agonists and yet do not stimulate or cause the level of circulating thyroid hormone to be chronically elevated above the normal range. These TSHR agonists are therefore useful for treating metabolic syndrome and other related metabolic diseases and disorders, such as obesity, in humans without inducing thyrotoxicosis.

Unexpectedly, according to the present disclosure, sialylated TSHR agonists as used in art-established rodent models of metabolic syndrome are not necessary for the treatment of metabolic syndrome in humans. As described herein, substantially desialylated TSHR agonists exhibit the capability to induce lipolysis in adult human adipocytes. Furthermore, a substantially desialylated TSHR agonist as provided herein can induce a potent lipolytic response in a subject without overstimulation of the thyroid. As herein disclosed, a substantially desialylated TSHR agonist may therefore acutely stimulate lipolysis in adipose tissue at doses that do not induce thyrotoxicosis in a subject.

As noted above, the use of TSHR agonists as lipolytic agents has been examined in rodent models of the metabolic syndrome. These agonists include corticotroph-derived glycoprotein hormone (CGH), also named thyrostimulin, and thyroid-stimulating hormone (TSH), also known as thyrotropin (see, e.g., U.S. Patent Application Publication Nos. 2004/0176294 and 2003/0095983). Treatment of rodents with TSH and CGH produced by recombinant DNA methods in Chinese hamster ovary (CHO) cells results in improved glucose and lipid profiles and in reversed liver steatosis. Rodent adipose tissue TSHRs are acutely activated by these glycoproteins and generate a strong lipolytic stimulus, increasing metabolic rate through acute elevation of serum FFAs. Lipolysis and metabolic benefits are produced at doses of 50-250 μg/kg/day administered by intraperitoneal (ip) injection (see, e.g., U.S. Patent Application Publication Nos. 2004/0176294 and 2003/0095983).

Even though the results described in the rodent models suggest that TSHR agonists may be useful therapeutics for metabolic syndrome, treatment of humans with these agonists presents several problems. The extended half-life of recombinant TSH in primates suggests that lipolytic doses of recombinant TSH will produce an undesirable hyperthyroid state. Additionally, administration of TSHR agonists to humans who are not hypothyroid leads to undesirable adverse effects (e.g., thyrotoxicosis) by causing excess stimulation of the thyroid, resulting in chronic elevation of serum thyroid hormone levels above the normal range.

Development of TSH-related therapeutics for use in humans has therefore focused on creating and developing long-lasting sialylated TSH glycoforms, despite data showing that desialyated TSH had greater intrinsic activity in vitro, because the desialyated forms are physiologically cleared from the circulation significantly faster and are therefore less active in vivo (see, e.g., Grossman et al., *Endocrine Rev.* 18:476-501 (1997); Szkudlinski et al., *Physiol. Rev.* 82:473-502 (2002); Thotakura et al., *Endocrinology* 128:341-48 (1998); Grossman et al., *Endocrinology* 138:92-100 (1997); U.S. Patent Application Publication Nos. 2004/0266665; 2005/0250185; and 2005/0096264). Intrinsic activity refers to the specific activity of a ligand for a receptor measured by potency of signal transduction per unit of molar mass of ligand, which is usually in an in vitro assay.

Furthermore, while the presence of TSH binding sites on extrathyroid tissues such as lymphocytes, testicular and adrenal tissue, and adipocytes has been known, the functional expression and physiological relevance of human TSH receptors and human TSH has not been established. As elaborated herein according to presently disclosed embodiments, and contrary to prior observations and conclusions in the art, the markedly increased metabolic clearance rate (MCR) of a substantially desialylated TSHR agonist, compared with that of a sialylated TSHR agonist, provides therapeutic benefit to a subject by permitting induction of lipolysis without induction of thyrotoxicosis.

As used herein, the term “isolated” means that a material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such a nucleic acid could be part of a vector and/or such nucleic acid or polypeptide could be part of a composition, and still be isolated in that the vector or composition is not part of the natural environment for the nucleic acid or polypeptide. The term “gene” refers to the segment of DNA that is transcribed in the process for producing a polypeptide chain; it includes regions preceding and following the coding region “leader and trailer” as well as intervening sequences (introns) between individual coding segments (exons).

As used herein and in the appended claims, the singular forms “a,” “and,” and “the” include plural referents unless the context clearly dictates otherwise. Thus, for example, reference to “an agent” includes a plurality of such agents, and reference to “the cell” includes reference to one or more cells and equivalents thereof known to those skilled in the art, and so forth. The term “comprising” (and related terms such as “comprise” or “comprises” or “having” or “including”) is not intended to exclude that, for example, any composition of matter, composition, method, or process, or the like, described herein may “consist of” or “consist essentially of” the described features.

Substantially Desialylated TSHR Agonists

Provided herein are compositions comprising substantially desialylated TSHR agonists for use in methods for treating metabolic syndrome in a subject. As described in detail herein, a substantially desialylated TSHR agonist is capable of increasing the intrinsic activity on adipose TSHRs for the induction of lipolysis. The metabolic clearance rate (MCR) of these agonists is sufficient to prevent or inhibit over-stimulation of the thyroid and thus prevent or reduce the likelihood that a subject treated subject with the substantially desialylated TSHR agonist will develop thyrotoxicosis.

The TSH receptor (TSHR) is a member of the G-protein coupled, seven-transmembrane receptor superfamily. Activation of the TSH receptor, for example, by specific binding or engagement of a TSHR agonist, leads to coupling with heterotrimeric G proteins, which evokes downstream cellular effects. The TSH receptor may interact with G proteins of several subtypes, including $G_s$, $G_q$, $G_{12}$, and $G_i$. In particular, interaction with $G_s$ may lead to activation of adenylate cyclase and increased levels of cAMP. See Laugwitz, K. L., et al. (1996) *Proc. Natl. Acad. Sci. USA* 93, 116-120.

The TSHR agonist polypeptides described herein include pituitary glycoprotein hormones, for example, TSH and CGH. These glycoprotein hormones comprise a carbohydrate moiety, usually of one, two, or three distinct asparagine (N)-linked oligosaccharides typically having predominantly biantennary structure (Grossman et al., *Endocrinol. Rev.* 18:476-501 (1997)). Historically, isoelectric focusing studies characterized oligosaccharide variants of glycoprotein hormones by relative acidity. Subsequent studies revealed that increased acidity of such variants was due to the presence of non-reducing terminal sulfate ($SO_4$) covalently linked to penultimate N-acetylgalactosamine (GalNAc) residues, and/or to the presence of the oligosaccharide non-reducing termini of sialic acid (NeuAc) groups covalently linked to penultimate galactose residues on the N-linked oligosaccharide moiety.

TSHR agonists, including desialylated TSHR agonists, specifically interact with and/or specifically bind to TSHR to stimulate or activate a signal that is transduced intracellularly and that elicits a biological response. By way of example, binding of TSH to the TSH receptor on adipocytes stimulates second messenger pathways that involve alterations (e.g., statistically significant increases or decreases) in cAMP levels and that may ultimately alter gene expression. Activation of TSHR present on adipocytes may result in lipolysis, which can be analyzed by determining accumulation of glycerol and free fatty acids (FFA), using methods described herein and practiced in the art. A desialylated TSHR agonist may competitively inhibit binding of TSH to TSHR, or such an agonist may bind to TSHR at a different binding site than does TSH. A desialylated TSHR agonist may also include an agonist that binds to TSHR at two different sites; for example, one site may include a TSH binding site, and a second site may be a different and distinct binding site such that binding of the desialylated TSHR agonist does not inhibit binding of TSH to the TSH receptor (see, e.g., Okada et al., *Mol. Endocrinol.* Oct. 6, 2005 (Epub ahead of print)).

As used herein, a TSHR agonist is said to be “specific for” or to “specifically bind” to a TSHR if it reacts at a detectable level with the receptor, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$, and that does not specifically bind to another cell surface receptor. Affinity of an agonist for its cognate receptor is also commonly expressed as a dissociation constant $K_D$, and a TSHR agonist specifically binds to TSHR if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of binding partners can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.) and by other methods routinely practiced in the art (see, e.g., Wolff et al., *Cancer Res.* 53:2560-2565 (1993).

In particular embodiments, methods described herein for treating metabolic syndrome and related metabolic diseases and disorders in a subject, comprise administering a desialylated TSHR agonist that is non-immunogenic in the subject. In certain embodiments, the desialylated TSHR agonist is an autologous desialylated TSHR agonist; that is, the desialylated TSHR agonist is derived from the same species as the subject to be treated. In other embodiments, the desialylated TSHR agonist may be from a heterologous source, and the agonist may be modified in a manner to reduce or abrogate the immunogenicity (e.g., decrease in a statistically significant or biologically significant manner relative to an unmodified control) of the heterologous desialylated TSHR agonist in the subject that is treated with the agonist. Modifications include but are not limited to substituting, deleting, or adding amino acids of an epitope of the agonist such that the immunogenicity of the agonist in a heterologous host or subject is reduced or abrogated. Introducing such mutations into the agonist polypeptide may be accomplished according to methods routinely practiced in the art. Alternatively, a heterologous desialylated TSHR agonist may be delivered prior to, concurrently, or subsequent to an agent or composition that is capable of suppressing an immune response in the host to the heterologous desialylated TSHR agonist.

Exemplary desialylated TSHR agonists are pituitary glycoprotein hormones that are substantially desialylated or are asialylated, including but not limited to desialylated thyroid-stimulating hormone (TSH) (also called thyrotropin) and corticotroph-derived glycoprotein hormone (CGH) (also called thyrostimulin or orphan glycoprotein hormone (OGH)). Human TSH is a ~30 kDa glycoprotein composed of two non-covalently linked peptide subunits: an alpha subunit and a beta subunit. The alpha subunit of TSH is the same as that of luteinizing hormone, follicle-stimulating hormone, and chorionic gonadotropin. Prior to cleavage of a signal peptide, the alpha subunit of TSH has the following amino acid sequence: MDYYRKYAAIFLVTLSVFLHVLHSAPDVQDCPECTLQENPFFSQPGAPILQCMGCCFSRAYPTPLRSKK TMLVQKNVTSESTCCVAKSYNRVTVMGGFKVENHTACHCSTCYYHKS (SEQ ID NO:1). The signal peptide is located at positions 1-24 (SEQ ID NO:5). The amino acids located at positions 25 to 116 of the alpha subunit (SEQ ID NO:1) comprise the mature protein (SEQ ID NO:6). The beta subunit of TSH is unique and has the following amino acid sequence: MTALFLMSMLFGLACGQAMSFCIPTEYTMHIERRECAYCLTINTTICAGYCMTRDINGKLFLPKYALSQDVCTYRDFIYRTVEIPGCPLHVAPYFSYPVALSCKCGKCNTDYSDCIHEAIKTNYCTKPQKSYLVGFSV (SEQ ID NO:2). The beta subunit of the glycoprotein determines the hormone's biological specificity. The beta subunit also comprises a signal peptide (SEQ ID NO:7) (positions 1-20 of SEQ ID NO:2). Amino acids located at positions 21 to 138 of SEQ ID NO:2 comprise the mature protein (SEQ ID NO:8).

A structural feature of glycoprotein hormones is their carbohydrate moiety, which may exhibit structural microheterogeneity within a population of glycoprotein molecules. Hence, TSH is secreted, not as a homogeneous population, but as a set of glycosylation variants (see, e.g., Szkudlinski M., et al. (2001) *Physiol Rev* 82, 473-502). The α-subunit has two asparagine (N)-linked oligosaccharides located in the mature α-subunit at amino acid sequence positions $N^{52}$ and $N^{78}$ (see SEQ ID NO:6). The β-subunit of TSH has a single N-linked oligosaccharide located at amino acid position $N^{23}$ of the mature polypeptide (see SEQ ID NO:8).

CGH is a heterodimeric glycoprotein protein composed of an alpha subunit called GPHA2 (SEQ ID NO 3) and a beta subunit called GPHB5 (SEQ ID NO. 4) (see, e.g., Nakabayashi et al., *J. Clin. Invest.* 109:1445-52 (2002); Okada et al., *Mol. Endocrinol*. Oct. 6, 2005 (Epub ahead of print); International Patent Application Publication No. WO 01/73034). The mature GPHA2 subunit (SEQ ID NO:10) is formed after cleavage of the signal peptide (SEQ ID NO:9) from the full length glycoprotein (SEQ ID NO:3). The GPHB5 subunit comprises a signal peptide (SEQ ID NO:11) (positions 1-24 of SEQ ID NO:4), and amino acids located at positions 25-130 of SEQ ID NO:4 comprise the mature GPHB5 subunit (SEQ ID NO:12). CGH contains two N-linked glycosylation sites on the α-subunit (see positions 14 and 58 of SEQ ID NO:10) and one N-linked glycosylation on the β-subunit (see position 63 of SEQ ID NO:12) (see Nakabayashi et al., *J. Clin. Invest.* 109:1445-52 (2002)).

CGH has not been purified from serum or tissues, but has been produced in hamster ovary (CHO) cells by recombinant DNA methodology to yield a purified heterodimeric protein that potently activates the human TSHR transfected into CHO cells. GPHA2 has an amino acid sequence that is 25% identical to the amino acid sequence of the alpha subunit common to other known glycoprotein hormones, and it is predicted to have similar structural motifs. GPHB5 has an amino acid sequence that is approximately 30% identical to the amino acid sequence of the beta subunit of human thyroid-stimulating hormone, and is also predicted to be structurally conserved.

In one embodiment, the TSHR agonist is a substantially desialylated glycoprotein comprising at least one N-linked oligosaccharide chain (i.e., an N-linked oligosaccharide moiety) that is substantially desialylated or that is not sialylated. In certain embodiments, the TSHR agonist comprises at least two, at least three, or more N-linked oligosaccharide chains. As described herein, an oligosaccharide moiety (also called herein an oligosaccharide chain or oligosaccharide isoform) of a TSHR agonist is an N-linked oligosaccharide chain of predominantly biantennary structure. These oligosaccharide chains are comprised of the sugars mannose, fucose, N-acetylgalactosamine, N-acetylglucosamine, and galactose (see, e.g., Grossman et al., *Endocrine Reviews* 18:476-501 (1997); Harvey, *Proteomics* 5:1774-86 (2005); Schauer, *Zoology* (*Jena*) 107:49-64 (2004); Schauer *Glycoconj. J.* 17:485-99 (2000)). The chains may also be terminated (e.g., at the non-reducing terminus) with sulfate ($SO_4$) or sialic acid. Thus, in certain embodiments, the desialylated TSHR agonists include N-linked high-mannose oligosaccharides. Certain TSHR agonists, such as TSH and CGH, have three biantennary N-linked oligosaccharide chains, each of which could possess sialic acid as the non-reducing terminal carbohydrate residue for a possible total of six sialic acid molecules per molecule of glycoprotein. By way of example, a substantially desialylated TSH or substantially desialylated CGH, has only one or has only two sialic acid molecules per agonist molecule. In a specific embodiment, the substantially desialylated TSHR agonist is asialylated (i.e., each N-linked oligosaccharide moiety lacks sialic acid as an end group).

In other embodiments, the substantially desialylated TSHR agonist comprises a glycoprotein preparation comprising one or more (i.e., a plurality) of glycoprotein molecules, each of which has at least one, two, three, or more N-linked oligosaccharide moieties. In certain embodiments, the substantially desialylated TSHR agonist comprises a glycoprotein preparation that is at least 85%, 90%, 95%, or 98% desialylated. The glycoprotein preparation may comprise glycoprotein molecules wherein each glycoprotein molecule exhibits the same percent desialylation. Alternatively, the glycoprotein preparation may comprise glycoprotein molecules that exhibit differing percent desialylation, such that the combination of such glycoprotein molecules in the preparation is at least 85%, 90%, 95%, or 98% desialylated. In another embodiment, the substantially desialylated TSHR agonist comprises a glycoprotein preparation that lacks detectable sialic acid and that may be asialylated (i.e., each N-linked oligosaccharide moiety lacks a sialic acid end group). In another embodiment, the substantially desialylated TSHR agonist comprises a glycoprotein preparation that is at least 70%, 75%, or 80% desialylated. In a particular embodiment, for example, the TSHR agonist comprises a TSH glycoprotein preparation, and in another particular embodiment, the TSHR agonist comprises a CGH glycoprotein preparation. In still another embodiment, the TSHR agonist comprises a mixture of glycoprotein preparations, such as a first glycoprotein preparation and a second glycoprotein preparation. In one embodiment, each of the first glycoprotein preparation and the second glycoprotein preparations is at least 85%, 90%, 95%, or 98% desialylated, or at least 70%, 75%, or 80% desialylated, or may lack detectable sialic acid. In another certain embodiment, the combination or mixture of at least one glycoprotein preparation and at least one second glycoprotein preparation together is at least 85%, 90%, 95%, or 98% desialylated, or at least 70%, 75%, or 80% desialylated, or may lack detectable sialic acid. In a particular embodiment, a mixture of glycoprotein preparations comprises a TSH glycoprotein preparation and a CGH glycoprotein preparation.

The presence of and/or quantification of sialic acid molecules bound to an oligosaccharide moiety of a TSHR agonist may be determined according to methods described herein and that are known to persons skilled in the art. For example, *Ricinus communis* binds specifically to exposed galactose residues, and the presence of sialic acid attached to galactose prevents such binding. A glycoprotein, such as a TSHR agonist, is combined with neuraminidase, which cleaves sialic acid residues and thus exposes galactose. The degree or extent of sialylation (i.e., the number or the average number of sialic acid molecules per unit mass, for example) is correlated with and can be determined by measuring the increase in binding of the glycoprotein to ricin (see, e.g., Oliveira et al., *J. Clin. Endocrinol. Metab.* 86:1694-99 (2001)). According to another exemplary method, a glycoprotein is treated with sialidase or subjected to mild acid hydrolysis, before being treated with N-acetylneuraminic acid aldolase, which converts the free sialic acid residues to their corresponding N-acylmannosamines (see, e.g., Yasuno et al., *Biosci. Biotechnol. Biochem.* 63:1353-59 (1999)). The reaction mixture is then successively subjected to acid hydrolysis (in order to produce monosaccharides), N-acetylation, and conversion with ρ-aminobenzoic acid ethyl ester (ABEE). The ABEE-converted monosaccharides are simultaneously determined by reverse-phase high-performance liquid chromatography. Other methods incorporate additional techniques, for example, capillary electrophoresis, which may be combined with ion-trap mass spectrometry (see, e.g., Che et al., *Electrophoresis* 20:2930-37 (1999) and anion exchange HPLC (see, e.g., Dionex, Sunnyvale, Calif.; see also, e.g., Harvey, *Proteomics* 5:1774-86 (2005); Duk et al., *Adv. Exp. Med. Biol.* 491:127-32 (2001); Varke et al., *Anal. Biochem.* 137: 236-47 (1984)).

Substantially desialylated TSHR agonists (e.g., CGH and TSH) include polypeptide variants, as elaborated below, of the respective desialylated TSHR agonist. For certain desialylated TSHR agonist variants, the biological activities are enhanced or are unchanged compared to the native desialylated TSHR agonist. The capability of such a variant to induce lipolysis in adipocytes is not substantially diminished and the capability of the variant to induce thyrotoxicosis is not substantially increased (i.e., the biological activity of the agonist variant is not altered in a statistically or biologically significant manner that adversely alters the biological function of the desialylated TSHR agonist). The capability of such a desialylated TSHR agonist variant to induce lipolysis in adipocytes (e.g., human adipocytes) may be enhanced or unchanged, relative to a native desialylated TSHR agonist, or may be diminished by less than 50%, less than 40%, than 30% or 25%, less than 20%, or less than 10%, relative to the agonist. Such variants may be identified using the representative assays and techniques provided herein.

Substantially desialylated TSHR agonists, including TSH and CGH described herein, thus also include variants or each respective glycoprotein hormone, and which variants have a similar amino acid sequence to the TSH and CGH amino acid sequences disclosed herein. Such polypeptide variants may contain one or more substitutions, deletions, additions and/or insertions. Variants include, for example, naturally occurring polymorphisms (e.g., allelic variants) or recombinantly manipulated or engineered TSHR agonist variants. The amino acid sequence of a substantially desialylated TSHR agonist variant (or a subunit thereof) is at least 70%, 75%, 80%, 85%, 90%, 95%, or 98% identical or similar to the native agonist (or subunit thereof). In a specific embodiment, the amino acid sequence of the alpha subunit of a substantially desialylated TSH variant is at least 70%, 75%, 80%, 85%, 90%, 95%, or 98% identical or similar to the sequence set forth in SEQ ID NO:1 or SEQ ID NO:6. In another specific embodiment, the amino acid sequence of the beta subunit of a substantially desialylated TSH variant is at least 70%, 75%, 80%, 85%, 90%, 95%, or 98% identical or similar to the sequence set forth in SEQ ID NO:2 or SEQ ID NO:8. In still another specific embodiment, the amino acid sequence of the alpha subunit of a substantially desialylated CGH variant is at least 70%, 75%, 80%, 85%, 90%, 95%, or 98% identical or similar to the sequence set forth in SEQ ID NO:3 or SEQ ID NO:10. In another specific embodiment, the amino acid sequence of the beta subunit of a substantially desialylated CGH variant is at least 70%, 75%, 80%, 85%, 90%, 95%, or 98% identical or similar to the sequence set forth in SEQ ID NO:4 or SEQ ID NO:12.

A variety of criteria known to persons skilled in the art indicate whether amino acids at a particular position in a peptide or polypeptide are conservative or similar. For example, a similar amino acid or a conservative amino acid substitution is one in which an amino acid residue is replaced with an amino acid residue having a similar side chain, such as amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, histidine); nonpolar side chains (e.g., alanine, valine, leucine, isoleucine, proline, phenylalanine, methionine, tryptophan); beta-branched side chains (e.g., threonine, valine, isoleucine), and aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. The percent identity or similarity between two TSHR agonists having an amino acid sequence can be readily determined by alignment methods (e.g., using GENEWORKS, Align or the BLAST algorithm), which are also described herein and are familiar to a person having ordinary skill in the art.

A substantially desialylated TSHR agonist variant may also be readily prepared by genetic engineering and recombinant molecular biology methods and techniques. Briefly, analysis of the primary and secondary amino acid sequence of an agonist and analysis by computer modeling to analyze the tertiary structure using the amino acid sequence and canonical structures and motifs of the polypeptide may aid in identifying specific amino acid residues that can be substituted, including computer-assisted prediction of sequence variants' structure (Bradley et al., *Science* 309:1868 (2005); Schueler-Furman et al., *Science* 310:638 (2005)). In addition, evolutionary conservation of or tolerance for amino acid variability in related polypeptides may provide insight into amino acid residues that may be altered to reduce, maintain, or enhance activity. Amino acid substitutions that may not be desirable in the desialylated TSHR agonists described herein include substitutions of amino acids of an agonist, such as substitution of particular residues in TSH, described by Leitolf et al. (*J. Biol. Chem.* 275:27457-65 (2000); (see also, e.g., U.S. Patent Application Publication No. 2004/0266665)) that increase an intrinsic activity on thyroid cells, for example, signal transduction activity, but that also increase the serum half-life of the agonist and/or decrease the MCR. Accordingly, in certain embodiments, a TSH variant comprising one or more specific amino acid substitutions, insertions, and/or deletions described in U.S. Patent Application Publication No. 2004/0266665 and Leitolf et al., supra, is excluded.

Modification of DNA encoding a TSHR agonist or fragment may be performed by a variety of methods, including site-specific or site-directed mutagenesis of the DNA, which methods include DNA amplification using primers to introduce and amplify alterations in the DNA template, such as PCR splicing by overlap extension (SOE). Mutations may be introduced at a particular location by synthesizing oligonucleotides containing a mutant sequence, flanked by restriction sites enabling ligation to fragments of the native sequence. Following ligation, the resulting reconstructed sequence encodes a variant (or derivative) having the desired amino acid insertion, substitution, or deletion.

Site-directed mutagenesis is typically effected using a phage vector that has single- and double-stranded forms, such as an M13 phage vector, which is well known and commercially available (see, e.g., Veira et al., *Meth. Enzymol.* 15:3 (1987); Kunkel et al., *Meth. Enzymol.* 154:367 (1987)) and in U.S. Pat. Nos. 4,518,584 and 4,737,462). Oligonucleotide-directed site-specific (or segment specific) mutagenesis procedures may be employed to provide an altered polynucleotide that has particular codons altered according to the substitution, deletion, or insertion desired. Deletion or truncation derivatives of proteins may also be constructed by using convenient restriction endonuclease sites adjacent to the desired deletion. Exemplary methods of making the alterations set forth above are disclosed by Sambrook et al. (*Molecular Cloning: A Laboratory Manual,* 3d ed., Cold Spring Harbor Laboratory Press, NY 2001). Alternatively, random mutagenesis techniques, such as alanine scanning mutagenesis, error prone polymerase chain reaction mutagenesis, and oligonucleotide-directed mutagenesis may be used to prepare TSHR agonist variants and fragment variants (see, e.g., Sambrook et al., supra).

In addition to above-described computational prediction of polypeptide variant three-dimensional structure (Bradley et al., supra; Schueler-Furman et al., supra), confirmatory assays for assessing whether the variant folds into a conformation comparable to the non-variant polypeptide or fragment may include, for example, testing the ability of the variant protein to react with mono- or polyclonal antibodies that are specific for native or unfolded epitopes, assessing retention by the variant protein of ligand-binding functions, and determining the sensitivity or resistance of the mutant (i.e., variant) protein to digestion with proteases (see Sambrook et al., supra). Substantially desialylated TSHR agonist variants as described herein can be identified, characterized, and/or made according to these methods described herein or other methods known in the art (e.g., functional assays such as assays for induction of lipolysis cAMP etc.), which are routinely practiced by persons skilled in the art.

Mutations that are made or identified in the nucleic acid molecules encoding a TSHR agonist polypeptide, for purposes of recombinant expression of the agonist, preferably preserve the reading frame of the coding sequences. By way of example, a polynucleotide variant may include a variant of a polynucleotide that comprises the nucleotide sequence, SEQ ID NO:13, that encodes the human TSH alpha subunit or SEQ ID NO:14 that encodes the human TSH beta-subunit, respectively. As another example, a polynucleotide variant may include a variant of a polynucleotide that comprises the nucleotide sequence, SEQ ID NO:15, that encodes the human CGH GPHA2 subunit or SEQ ID NO:16 that encodes the human CGH GPHB5 subunit, respectively. Furthermore, the mutations will preferably not create complementary regions that when transcribed could hybridize to produce secondary mRNA structures, such as loops or hairpins, that would adversely affect translation of the mRNA. Although a mutation site may be predetermined, the nature of the mutation per se need not be predetermined. For example, to select for optimum characteristics of a mutation at a given site, random mutagenesis may be conducted at the target codon and the expressed mutants screened for gain or loss or retention of biological activity.

Polynucleotide variants, which may be degenerate variants or which may include a polynucleotide variant that encodes a polypeptide variant, may also be identified by hybridization methods. Suitable moderately stringent conditions include, for example, pre-washing in a solution of 5×SSC, 0.5% SDS, 1.0 mM EDTA (pH 8.0); hybridizing at 50° C.-70° C., 5×SSC for 1-16 hours; followed by washing once or twice at 22-65° C. for 20-40 minutes with one or more each of 2×, 0.5×, and 0.2×SSC containing 0.05-0.1% SDS. For additional stringency, conditions may include a wash in 0.1×SSC and 0.1% SDS at 50-60° C. for 15 minutes. As understood by persons having ordinary skill in the art, variations in stringency of hybridization conditions may be achieved by altering the time, temperature, and/or concentration of the solutions used for pre-hybridization, hybridization, and wash steps. Suitable conditions may also depend in part on the particular nucleotide sequences of the probe used (i.e., for example, the guanine plus cytosine (G/C) versus adenine plus thymidine (A/T) content). Accordingly, a person skilled in the art will appreciate that suitably stringent conditions can be readily selected without undue experimentation when a desired selectivity of the probe is identified.

Preparation of Substantially Desialylated TSHR Agonist Glycoforms

Substantially desialylated TSHR polypeptide agonist glycoforms may be produced by biopharmaceutical methods and techniques practiced by persons having ordinary skill in the art. A TSHR agonist may be obtained from commercial sources and then desialylated. By way of example, TSH may be obtained from commercial sources, such as Genzyme Corporation (Thyrogen®, Cambridge, Mass.), and treated enzymatically to produce desialylated TSH. Removal of sialic acid moieties is a technique well known to skilled practitioners in the art and may be readily performed using established chemical and/or enzymatic procedures (see, e.g., Varke et al., supra; Duk et al., supra) including the use of commercially available neuraminidase or sialidase reagents (see, e.g., Sigma-Aldrich, St. Louis, Mo.). These reagents are also readily available as agarose conjugates. See Thotakura, N., et al. (1991) *Endocrinology* 128, 341-348.

In another embodiment, a TSHR agonist, such as CGH or TSH, may be produced by recombinant expression methods. Recombinant expression vectors comprising genes that encode the respective α-subunit and β-subunit of a TSHR agonist glycoprotein may be inserted into cultured mammalian CHO cells according to standard molecular biology methods routinely practiced in the art, followed by purification of the TSHR polypeptide agonists from the cells or from conditioned cell culture media. See, e.g., International Patent Application Publication No. WO 03/006051. The sialylated TSHR agonist is then de-sialylated as described herein using sialidase reagents to produce a substantially desialylated TSHR agonist polypeptide glycoform with high intrinsic activity at adipose TSHRs and with lower serum half-life to avoid thyrotoxicosis. Skilled persons in the art will readily appreciate that several mammalian cell hosts, vectors, and purification methods can be used to produce purified substantially desialylated TSHR polypeptide agonists (see, e.g., U.S. Patent Application Publication Nos. 2003/0095983, 2003/0207403; see generally Sambrook et al., *Molecular Cloning: A Laboratory Manual,* 3d ed., Cold Spring Harbor Laboratory Press, NY (2001)).

A substantially desialylated TSHR agonist, such as substantially desialylated CGH or substantially desialylated TSH, may be produced from mammalian cell culture under conditions that minimize the addition of sialic acid moieties to the oligosaccharide side chains (see, e.g., Szkudlinkski et al., *Endocrinology* 133:1490-1593 (1993)). TSHR polypeptide agonist glycoforms produced under defined culture conditions can have oligosaccharide side chains with none or a reduced number of sialic acid moieties. A TSHR agonist expressed in cell culture and that has a reduced number of sialic acid residues may be further desialylated enzymatically as described herein.

In yet another example, a substantially desialylated TSHR polypeptide agonist glycoform may be produced from mammalian cell culture using cell lines with defective oligosaccharide processing pathways. For example, CHO-LEC2 cells (Invitrogen, Carlsbad, Calif.) are defective in sialic acid transport and secrete glycoproteins lacking terminal sialic acids. Another exemplary cell line comprises CHO mutant cells that are deficient in N-acetylglucosamine transferase-I enzyme activity. This mutant cell line secretes glycoproteins with N-linked (GlcNAc)2(Mannose)5 oligosaccharides, lacking terminal sialic acid. See Galway, A B., et al. (1990) *Endocrinology* 127, 93-100. A practitioner skilled in the art will recognize that any one or more other of cell lines having mutations and/or defects in various pathways associated with oligosaccharide sialylation, including for example, sialic acid biosynthetic pathways, sialyl transferases, glycosyl hydrolases, glycoprotein processing, folding, chaperone proteins, and the like, could be used to produce sialic-acid deficient TSHR agonists (e.g., substantially desialylated CGH or substantially desialylated TSH glycoproteins).

Substantially desialylated TSHR polypeptide agonist glycoforms may, for example, be produced in cells that do not terminate oligosaccharide chains with sialic acid residues. In one instance, TSHR polypeptide agonists may be produced in insect cells, using Baculovirus infection expression systems. Glycoproteins produced using these systems, especially with high-expression promoters, are secreted with high-mannose oligosaccharide chains. See Grossman, M. et al., (1997) *Endocrinology* 138, 92-100. In another instance, TSHR polypeptide agonist glycoforms may be produced in yeast cells by standard recombinant methods familiar to those skilled in the art. Yeast cells, for example, *Pichia pastoris* or *Saccharomyces cerevisiae*, secrete glycoproteins having high-mannose oligosaccharide chains, which are not sialylated. TSHR polypeptide agonist glycoforms may therefore be expressed in yeast cells to produce glycoproteins deficient in sialic acid-terminated oligosaccharides (i.e., substantially desialylated TSHR agonists as provided herein).

In another embodiment, substantially desialylated TSHR polypeptide agonist glycoforms may be produced in bacterial cell culture. Bacterial cell culture for the production of biopharmaceuticals is a skill well-known to practitioners in the art. Proteins produced in bacteria do not contain N-linked oligosaccharides, and therefore do not have sialylated oligosaccharides.

TSHRs in Human Adipose Tissue

The presence of TSH receptors in human adipose tissue has been the subject of controversy for some time, including suggestions that TSHRs were not present and/or were not functional in human fat (see, e.g., Davies et al., *N. Engl. J. Med.* 296:759-60 (1977); Grossman et al., 1997, supra). Recent reports have documented the expression of TSHR in adipose tissue of rodents (see, e.g., Endo, et al. (1995) *J Biol Chem* 270, 10833-10837). In rodents, TSHR activation in adipose tissue by TSH or CGH leads to increased expression of lipogenic genes and elaboration of adipose specific cytokines, such as adiponectin. Thus, in addition to the acute stimulation of lipolysis by TSH or CGH, the metabolic status of adipose tissue is apparently altered. However, TSHR polypeptide agonists presently used in the art (which are agonists other than the substantially desialylated TSHR agonists described herein) that have sialylated and sulfated oligosaccharides exhibit lower intrinsic lipolytic activity. Accordingly, therapeutic doses of such sialylated and/or sulfated TSHR agonists must, in order to be present at levels therapeutically effective for the treatment of metabolic syndrome, be administered in amounts that as an undesirable side-effect will produce a chronic hyperthyroid state in humans.

In marked contrast to the various embodiments presented herein, prior to the present disclosure, it was not appreciated that in the context of metabolic syndrome a preferred ligand glycoform for TSHR expressed in human adipose tissue should lack acidic endgroups on glycosyl side chains. As described herein, nonionic TSHR agonist glycoforms such as substantially desialylated TSHR agonists (and preparations thereof) may provide high intrinsic activity at adipose tissue TSHR effective to stimulate lipolysis, and thus such glycoforms will be unexpectedly useful for treating metabolic syndrome and/or obesity, and other metabolic diseases and disorders. Acute exposure to a substantially desialylated TSHR agonist, such as substantially desialylated TSH or substantially desialylated CGH, may therefore be sufficient to treat metabolic syndrome and other metabolic diseases and disorders. Surprisingly, in view of the rapid in vivo clearance of such desialylated glycoproteins from the circulation, the high intrinsic activity of substantially desialylated TSHR glycoforms at adipose tissue TSHRs can potently stimulate lipolysis while being administered for time periods and in amounts that will not over-stimulate the thyroid such that clinically detrimental side-effects of excessive thyroid stimulation, such as thyrotoxicosis, are thereby beneficially avoided.

Prior to the disclosure provided herein describing interaction between desialylated THSR agonists and adipose cells and tissue, the in vivo potency of TSH glycoforms (i.e., sialylated, asialylated, sulfated TSH, and mixtures thereof) was typically determined by measuring release into the circulation of thyroid hormone or by other measurements of thyroid function. Without wishing to be bound by theory, the prior art's lack of a direct correlation between in vitro and in vivo activities of TSH relates to differences between (i) mere characterization of interactions in vitro between distinct oligosaccharide isoforms with the thyroid TSHR, and (ii) the differential recruitment in vivo by such isoforms of carbohydrate-dependent clearance mechanisms, which determine the circulatory half-life of the glycoprotein. Further according to non-limiting theory, while sialylated forms of TSH have 4-20-fold lower intrinsic activity (i.e., in vitro activity) than non-sialylated glycoforms, such sialylated forms have significantly higher in vivo thyroid function potency due to a lower rate of serum clearance.

By way of brief background, in the context of beneficially altering thyroid function by administering TSH having sustained bioavailability through prolonged serum half-life, TSHR glycosylation isoforms have previously been studied for differences in serum half-life, or metabolic clearance rate (MCR). Investigations revealed that oligosaccharide isoforms of TSH having terminal sialic acid exhibited significantly decreased MCR (see, e.g., Szkudlinski et al., *Endocrinology* 133:1490-1053 (1993)). Removal of sialic acid moieties from sialylated isoforms by enzymatic methods to produce asialo glycoforms (asTSH) result in marked increase in MCR (see, e.g., Szkudlinski et al., supra). Asialylated TSH was cleared from serum 10-100 fold faster than sialylated TSH. Other studies showed that sulfated forms of glycoproteins had shorter serum half lives than fully sialylated isoforms, but longer than desialylated glycoforms. See Baenziger, J. et al. (1992) *PNAS* 89, 334-338. The rapid clearance and short half-life of desialylated forms TSH glycoforms were not regarded as offering therapeutic benefit for altering thyroid function. By way of contrast, according to presently disclosed compositions and methods for treatment of metabolic syndrome and related and/or associated metabolic diseases and disorders, the shorter serum half life and more rapid clearance of a substantially desialylated TSHR agonist provides a wholly unexpected therapeutic advantage.

Thus, according to the instant disclosure, a rapid, potent lipolytic response is produced without causing sustained over-stimulation of the thyroid. Not wishing to be bound by any particular theory, a subject may therefore avoid a detrimental hyperthyroid state (e.g., leading to thyrotoxicosis), at least in part, because administration (such as by injection) of lipolytic doses of a substantially desialylated TSHR agonist (e.g., substantially desialylated TSH or substantially desialylated CGH) (i.e., acute exposure of exogenous TSHR agonist) suppresses release of endogenous thyroid hormones, such as TSH.

Methods for Treating Metabolic Syndrome and Other Metabolic Diseases and Disorders Provided herein are methods for treating metabolic syndrome in a subject. A subject in need of such treatment may be a human or may be a non-human primate or other animal (i.e., veterinary use) who has developed symptoms of metabolic syndrome or a related metabolic disease or disorder, or who is at risk for developing metabolic syndrome or a related metabolic disease or disorder. Examples of non-human primates and other animals include but are not limited to farm animals, pets, and zoo animals (e.g., horses, cows, buffalo, llamas, goats, rabbits, cats, dogs, chimpanzees, baboons, orangutans, gorillas, monkeys, elephants, bears, large cats, etc.).

A composition comprising a pharmaceutically acceptable carrier and a TSHR agonist that is substantially desialylated, as described herein, is administered to the subject under conditions and for a time sufficient to induce lipolysis in one or a plurality of adipocytes without inducing thyrotoxicosis in the subject. In certain embodiments, the composition is administered at an effective dose and in a manner, that is, under conditions and for a time sufficient, to provide an appropriate pharmacokinetic profile (e.g., serum half-life, MCR) that permits induction of lipolysis in adipocytes (which can be readily detected as described herein and known in the art, e.g., by FFA release into the circulation) while being cleared from the circulation in a time frame that avoids exposure to the thyroid at a level that induces or stimulates thyrotoxicosis (which can be readily detected as described herein and known to the art, e.g., by $T_4$:$T_3$ ratio). The substantially desialylated TSHR agonist is administered to provide an acute lipolytic stimulus, which is followed by a rapid return of the TSHR agonist to a baseline level within a range appropriate for the glycoprotein hormone. The methods described herein thus promote weight loss and/or treat metabolic syndrome without adverse medical sequelae related to the hyperthyroid state.

Thyrotoxicosis as used herein refers to a chronic hyperthyroid state that is indicated by excess levels of the thyroid hormones thyroxine ($T_4$) and triiodothyronine ($T_3$). The ratio of $T_4$ to $T_3$ in normal human serum is typically 100:1. Total thyroid hormone levels in a normal human range from 5-11 μg/dl of serum; this range is defined as the euthyroid state. Higher levels of thyroid hormones (thyrotoxicosis) result in a hyperthyroid condition, and lower levels of thyroid hormones in serum are defined as a hypothyroid state. As used herein, thyrotoxicosis or a hyperthyroid state is defined as a continuous presence of thyroid hormone levels above the normal range. Thyrotoxicity (e.g., thyrotoxicosis) can be monitored and determined by methods known in the art for determining levels of T4, or for determining the level of both T4 and T3.

Thyrotoxicosis as manifested clinically is characterized by one or more cardiovascular symptoms, including tachycardia and heightened blood pressure. Thus, a treated subject may also be monitored for physiological effects by a person skilled in the medical arts before and after administration of the presently disclosed compositions comprising a substantially desialylated TSHR agonist (including a glycoprotein preparation) as described in detail herein. For example, thyrotoxicity may be indicated by one or more of an abnormal heartbeat and heart rate, abnormally high metabolic rate, increased blood pressure, high body temperature, heat intolerance, irritability, and tremors of the fingers.

Metabolic syndrome (also called syndrome X) is typically associated with one or more metabolic disorders or abnormalities, including obesity. Metabolic syndrome may present with a cluster of metabolic disorders (metabolic abnormalities) and medical sequelae, which may include one or more of hypertension, type-2 diabetes, hyperlipidemia, dyslipidemia (high triglycerides (hypertriglyceridemia) and high cholesterol low-density lipoproteins (hypercholesterolemia)), insulin resistance, liver steatosis (steatohepatitis), hypertension, atherosclerosis, and other metabolic disorders. As used herein, a subject who is affected with metabolic syndrome may present at least one, two, three, four, or more of the metabolic disorders. In certain embodiments, the subject being treated for metabolic syndrome using the compositions and methods described herein may be obese or may have type 2 diabetes mellitus; in other embodiments, the subject may be both (i) obese and (ii) have type 2 diabetes mellitus.

As used herein, the terms "obesity" and "obesity-related" are used to refer to conditions of subjects who have a body mass that is measurably greater than ideal for their height and frame, which determination is made by persons trained in the clinical art. Body Mass index (BMI) is a measurement tool used to determine excess body weight, and is calculated from the height and weight of a subject. A human is considered overweight when the person has a BMI of 25-29; a person is considered obese when the person has a BMI of 30-39, and a person is considered severely obese when the person has a BMI of ≥40. Accordingly, the terms obesity and obesity-related refer to human subjects with body mass index values of greater than 30, greater than 35, or greater than 40.

Steatosis is the accumulation of fat deposits in the liver. Steatosis of any etiology can be associated with the development of fibrosis, which is referred to as steatohepatitis, and/or cirrhosis of the liver. Epidemiologic evidence suggests that obesity increases the risk of cirrhosis. For example, in an autopsy series, obesity was identified as the only risk factor for disease in 12% of cirrhotic subjects. See Yang, S. Q. et al. (1997) *Proc Natl Acad Sci USA* 94, 2557-2562. Notably, cirrhosis is approximately six times more prevalent in obese individuals than in the general population. In the United States, the high percentage of overweight people in the general population partially explains the fact that non-alcoholic fatty liver disease (NAFLD) is the most common liver disease. Type 2 diabetes is present in 33% of these subjects. The degree of obesity correlates positively with the prevalence and severity of fatty liver (steatosis), and this in turn correlates with steatohepatitis. A current explanation of the pathogenesis of steatohepatitis is the "two-hits" hypothesis. See Day, C. P, and James, O., *Gastroenterology* 114, 842-845. The first "hit" is the deposition of fat in hepatocytes, leading to fatty degeneration of the liver, or steatosis. This fatty degeneration increases the organ's sensitivity to the second "hit," which can be any one of a variety of insults including diabetes, lipid peroxidation due to drug metabolism, or excess alcohol intake. In certain embodiments, administration of at least one TSHR agonist that is substantially desialylated (or that is a preparation of glycoproteins) reverses accumulation of stored triglyceride in liver. A subject may be treated for 3, 6, or 12 weeks or longer to provide improvement in liver steatosis and/or to reduce damage from steatohepatitis. A skilled practitioner may use methods such as ultrasound imaging and/or determining levels of circulating liver enzymes to assess and monitor improvements in liver status.

Type 2 diabetes mellitus (Type 2 DM) is a common feature of metabolic syndrome. Type 2 DM typically refers to the type of diabetes that is diagnosed in patients older than 30 years of age, but it also occurs in children and adolescents. Clinically, Type 2 DM is characterized by hyperglycemia and insulin resistance. Type 2 DM is commonly associated with obesity, especially of the upper body (visceral/abdominal), and often occurs after weight gain. Type 2 DM is a heterogeneous group of disorders in which hyperglycemia results from both an impaired insulin secretory response to glucose and decreased insulin effectiveness to stimulate glucose uptake by skeletal muscle and restrain hepatic glucose production (insulin resistance). The resulting hyperglycemia may lead to other common conditions, such as obesity, hypertension, hyperlipidemia, and coronary artery disease.

The methods described herein for treating metabolic syndrome and for treating metabolic disorder related to or associated with metabolic syndrome, such as Type 2 DM, preferably may reduce (e.g., decrease with statistical or biological significance) blood glucose and insulin levels and improve insulin sensitivity (e.g., decrease insulin resistance). As described herein treatment may include prevention of or inhibition of an increase in the levels of blood glucose and/or insulin, that is, maintaining the blood levels of glucose and insulin within the normal range. Subjects who benefit from such treatment include subjects who have central obesity (excess fat around the waist). In certain embodiments, treatment of a patient with metabolic syndrome and/or Type 2 DM may include administration of other anti-diabetic compounds or drugs, such as for example, tolbutamide and chlorpropamide, and other drugs currently available for treating diabetes.

Thus, the methods described herein that comprises administering a substantially desialylated TSHR agonist (which includes a TSHR agonist glycoprotein preparation as described herein) may (i) promote lipolysis and thereby promote weight loss; and/or (ii) reduce (e.g., decrease or inhibit) liver steatosis; and/or (iii) increase insulin sensitivity. The methods described herein are also useful for treating type-2 diabetes or a pre-diabetic condition in a subject comprising administering a substantially desialylated TSHR agonist to the subject. Additionally, the substantially desialylated TSHR agonists described herein may be used for improving insulin sensitivity in a subject while maintaining (i.e., without disruption of) the hypothalamic-pituitary-thyroid (HPT) axis. In another embodiment, a substantially desialylated TSHR agonist may be administered according to the methods described herein to promote or induce reversal of steatosis or steatohepatitis.

The methods described herein may also be useful for the treatment of obesity. As described herein, the ability to stimulate lipolysis in adipose tissue provides a means of intervening in a large number of pathologies associated with obesity. In particular, a substantially desialylated TSHR agonist as described herein, when administered in vivo, may potently stimulate lipolysis without chronic over-stimulation of the thyroid. As a consequence, metabolic rate is increased, which may result in or lead to decreased weight, increased insulin sensitivity, and decreased serum hyperlipidemia. This increase in metabolism is independent of the activation of the HPT axis. In certain particular embodiments, the subject being treated with the substantially desialylated compositions described herein is not hypothyroid.

When used to promote, induce, stimulate, or maintain lipolysis, a substantially desialylated TSHR agonist can promote or initiate weight loss. The methods described herein are thus useful for treating metabolic disorders and conditions that include obesity, atherosclerosis associated with obesity or dyslipidemia, diabetes, hypertension associated with obesity or diabetes, steatosis or steatohepatitis, or more generally the various pathologies associated with obesity, without overstimulation of the thyroid. For treating obesity, or for promoting or maintaining weight loss, a subject may also be treated with other agents, medicaments, or drugs that induce weight loss.

The compositions and methods described herein are also useful for treating non-insulin dependent diabetes, in particular diabetes associated with obesity. In one embodiment, the use of a substantially desialylated TSHR agonist to treat non-insulin dependent diabetes is contemplated for use in non-obese individuals. The methods comprising administering a substantially desialylated TSHR agonist may also be used for treating dyslipidemias, including hypercholesterolemia and hypertriglyceridemia.

Also provided herein are methods for altering (increasing or decreasing in a statistically significant or biologically significant manner) a metabolic activity in a subject. Such a method comprises administering to the subject a composition that includes a pharmaceutically acceptable carrier and a TSHR agonist that is substantially desialylated. Administration of the composition is undertaken under conditions and for a time sufficient to alter the at least one metabolic activity in the subject without inducing thyrotoxicosis. In certain embodiments, altering the metabolic activity may comprise decreasing (or lowering or reducing) the level of blood sugar in a subject. As described herein, subjects with Type 2 DM exhibit hyperglycemia (high blood glucose), due to decreased effectiveness of insulin and/or decreased production of insulin. The level of glucose in the blood (or serum) of a subject can be readily measured either by the subject using any one of the commonly prescribed and/or commercially available glucose monitoring kits, or by a skilled clinician in a laboratory using standard methods available in the art. By administering to the subject in need thereof a composition comprising a substantially desialylated TSHR agonist (such as desialylated TSH or desialylated domed-CGH or a glycoprotein preparation as described in detail herein), insulin sensitivity may be improved or increased and/or insulin resistance decreased (or reduced, diminished, or inhibited). An insulin-sensitizing effect may be more readily detectable than an anti-obesity effect. Stimulation of fat oxidation may rapidly lower the intracellular concentration of metabolites that modulate insulin signaling. By contrast, the anti-obesity effect may develop gradually as large stores of fat are oxidized.

In another embodiment, a metabolic activity that is altered is the level of serum triglycerides in a subject. In a particular embodiment, the level of serum triglyceride in the subject is lowered or decreased (or reduced). In other embodiments, the compositions described herein are administered to prevent elevation or increase of the level of triglycerides in a subject. Such a subject may be, for example, at risk for developing cardiac disease, such as a subject who has metabolic syndrome or who has one or more of the metabolic disorders associated with metabolic syndrome. An elevated triglyceride level (which typically is measured in blood or serum) refers to the level that is above the normal range as determined according to standard clinical practice by persons skilled in the clinical art.

In still another embodiment, the metabolic activity that is altered is the metabolic rate. In a particular embodiment, the methods described herein that comprise administering a desialylated TSHR agonist, increase metabolic rate (particularly the resting metabolic rate (RMR)) in a subject and thus increase energy expenditure (or utilization) in the subject. Energy expenditure represents one side of the energy balance equation. In order to maintain stable weight, energy expenditure should be in equilibrium with energy intake. Much of the energy expended on a daily basis derives from RMR, which comprises 50-80% of the total daily energy expenditure. Methods for monitoring lipid metabolism and energy expenditure include but are not limited to calorimetry (direct (measurement of total heat production) or indirect (e.g., oxygen consumption)) examination of regional subcutaneous lipid composition (an index of lipid metabolism) by near-IR spectrometry and surface energy expenditure by infrared imaging (i.e., to measure surface temperature) (see, e.g., Buice et al., *Cell. Mol. Biol.* (Noisy-le-grand) 44:53-64 (1998); Mansell et al., *Am. J. Physiol.* 258 R1347-R1354 (1990)).

As described herein, methods are provided for inducing or producing lipolysis and increasing metabolic rate in humans without induction of a chronic hyperthyroid state. Unexpectedly, changes in adipose tissue gene expression follow the lipolytic stimulus by a substantially desialylated TSHR polypeptide agonist that activates TSHR present in adipocytes, thus altering the endocrine status of adipose tissue. Increased expression of regulators of lipogenesis such as Peroxisome Proliferator-Activator Receptor $\gamma$ (PPAR$\gamma$), and Glucose transporter 4 (GLUT4), as well as altered adipose cytokine (adipokine) expression are observed following the lipolytic stimulus. Increased expression of the adipokine adiponectin is associated with improvements in aspects of the metabolic syndrome such as obesity and impaired glucose tolerance. These actions occur through adiponectin action on liver and muscle (see, e.g., Guan et al., *Nat. Med.* 8:1122-28 (2002)). Determining levels of expression of adiponectin and/or other secreted adipose genes and/or gene products referred to as adipokines, which also includes leptin and resistin, as well as cytokines TNF-$\alpha$ and IL-6, may be useful for characterizing and monitoring lipolysis in a subject treated with the desialylated TSHR agonists described herein. Levels of expression of other genes and gene products, for example, the transcription factor sterol regulatory element binding protein (SREPB), which is a regulator of lipogenesis, fatty acid binding protein-1 (FABP-1), fatty acid synthase (FASN), suppressor of cytokine signaling (SOCS), and the insulin receptor, may also be determined. Methods for determining gene expression (for example, solution hybridization methods (e.g., BADGE (beads array for the detection of gene expression)) and gene product expression (e.g., immunochemical techniques and functional assays) are known to and routinely practiced by persons skilled in the art.

Strategies previously practiced for therapeutically inducing lipolysis have lacked specificity, such as using $\beta$-AR agonists in general, or have lacked efficacy, as observed when treating with the most specific $\beta_3$-AR agonists developed to date. In spite of the emphasis on development of $\beta_3$-AR-specific agonists, recent human studies have implicated the $\beta_1$- and $\beta_2$-adrenoreceptors as primary mediators of sympathetically induced thermogenesis and energy expenditure. While certain studies in human obese populations suggest that decreases in resting metabolic rate observed in these individuals are the result of impaired function of $\beta_2$-adrenoreceptors in adipose tissue (see, e.g., Schiffelers, S. L., et al. (2001) *J Clin Endocrinol Metab* 86, 2191-2199, and Blaak, E. E., et al. (1993) *Am J Physiol* 264, E11-17), other studies conclude that the accumulation of fat in obese subjects may be due to a defect in adipose tissue lipolysis rather than to defects in lipid utilization because increases in plasma FFA levels lead to increases in lipid oxidation and energy expenditure in human lean and obese subjects (see, e.g., Schiffelers, S. L., et al. (2001) *Int J Obes Relat Metab Disord* 25, 33-38).

As described herein, lipolysis is the biochemical process by which stored fats in the form of triglycerides are released from fat cells as individual free fatty acids (FFA) into the circulation. Lipolysis may be analyzed and characterized by determining the level of glycerol and/or free fatty acids (FFA) in a biological sample according to methods that are well known and routinely practiced in the biochemical and clinical art (see, e.g., U.S. Patent Application Publication No. 2004/0176294; see also, e.g., Wako NEFA C kit (Wako Chemicals GmbH, Neuss, Germany); Jebens et al., *Scand. J. Clin. Lab. Invest.* 52:717 (1992); Richieri et al., *Mol. Cell. Biochem.* 192:87-94 (1999) and references cited therein)). For example, the level of glycerol and/or FFA may be determined in serum obtained from a subject to whom the substantially desialylated TSHR agonist (or glycoprotein preparation thereof) has been administered.

In an embodiment, the substantially desialylated TSHR agonist stimulates lipolysis with an $EC_{50}$ of 0.5, 1, 5, or 10 nM (or any concentration within the aforementioned concentrations). In certain other embodiments, desialylated TSHR agonist stimulates lipolysis with an $EC_{50}$ of 0.01, 0.05, 0.1, 0.2, 0.4 nM or 15, 20, 25, or 50 nM (or any concentration within the aforementioned concentrations). Administration of exogenous substantially desialylated TSHR agonist to a subject at a dose range of 5-50 μg/kg produces sufficient exposure to adipose tissue TSHR to acutely stimulate lipolysis (see Example 2).

A biological sample includes but is not limited to blood, serum, plasma, fat tissue. A biological sample may be a blood sample (from which serum or plasma may be prepared), biopsy specimen (such as intra-abdominal or subcutaneous fat tissue), body fluids (e.g., lung lavage, ascites, mucosal washings, synovial fluid), tissue explant, organ culture, bone marrow, lymph nodes, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture, or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

Pharmaceutical Compositions and Administration of Pharmaceutical Compositions

Provided herein are pharmaceutical compositions comprising at least one substantially desialylated TSHR agonist as described herein. In certain embodiments, a pharmaceutical composition comprises at least one TSHR agonist that comprises at least one glycoprotein that has at least one N-linked oligosaccharide moiety that is substantially desialylated. For example, the pharmaceutical composition may comprise TSH that is substantially desialylated or may comprise CGH that is substantially desialylated or may comprise a combination or mixture of TSH and CGH, each of which is substantially desialylated. In certain other embodiments, the substantially desialylated TSHR agonist comprises a glycoprotein preparation that comprises one or a plurality of glycoprotein molecules, each of which has at least one or at least two or at least three N-linked oligosaccharide moieties, wherein the TSHR agonist is a glycoprotein preparation (e.g., TSH or CGH or both) that is at least 85%, 90%, 95%, or at least 98% desialylated, or is asialylated (or any percent between 85% and 100%).

As described herein, administration to a subject of a substantially desialylated TSHR agonist induces a potent lipolytic response in the subject; however, the level of the desialylated TSHR agonist in the subject (as measured, for example, by the level of the agonist in serum) is reduced, particularly over time due to the high MCR of the agonist, such that the thyroid is not over-stimulated. A dose that is effective for treating or preventing metabolic syndrome or an associated or related metabolic disease or disorder or for altering a metabolic activity as described herein may be cleared from the subject, as determined by concentration in a biological sample, such as blood or serum, to physiologically normal levels or below such levels within 4 hours, within 6 hours, or within 8 hours of administration of the substantially desialylated TSHR agonist to the subject. Normal physiologically levels of a TSHR agonist in serum of the subject is approximately 0.16-1.2 ng/ml, or may be within the range of 0.1-2.0 ng/ml.

Dosage of a composition comprising at least one substantially desialylated TSHR agonist, including a glycoprotein preparation, as described in detail herein, ranges from about 0.001 mg to about 1 mg per kilogram of body weight per day, or may range from about 0.01 μg to about 1 μg or from about 1 mg to about 10 mg per kilogram of body weight per day (including any integer or fraction of an integer between these doses). Exemplary doses include 5, 10, 20, 25, 30, 40, 50, or 75 μg/kg per day. However, the doses may be higher or lower as can be determined by a medical doctor with ordinary skill in the art. The dose of the compositions may differ, depending upon the patient's (e.g., human) condition, that is, stage of the disease, general health status, age, and other factors that a person skilled in the medical art will use to determine dose. A practitioner skilled in the art can determine and evaluate an effective or therapeutic dose of a TSHR agonist as described herein in a preferred carrier or excipient, for example, by determining whether the subject has an acute increase in circulating FFA and insulin when the subject is in the fasting state. Further, an effective therapeutic dose minimizes, inhibits, or prevents, chronic elevation of thyroid hormone levels above the normal range. Titration of dosage may be necessary to obtain a treatment level within the therapeutic dose range. For a complete discussion of drug formulations and dosage ranges see *Remington's Pharmaceutical Sciences,* 17th Ed., (Mack Publishing Co., Easton, Pa., 1990), and *Goodman and Gilman's: The Pharmacological Basis of Therapeutics,* 9th Ed. (Pergamon Press 1996).

Pharmaceutical compositions may be administered in a manner appropriate to the disease or disorder to be treated (or prevented) as determined by persons skilled in the medical art. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome (e.g., increased insulin sensitivity, weight loss), or longer disease-free and/or overall survival, or a lessening of symptom severity). Improved clinical outcome may be determined, for example, by assessing blood lipid levels, glucose levels, and insulin levels according to conventional methods and techniques available to persons in a clinical laboratory. Circulating thyroid hormone levels may also be determined according to methods practiced in the art to monitor and determine that the treated subject does not have or is not developing thyrotoxicosis. For prophylactic use, a dose should be sufficient to prevent, delay the onset of, or diminish the severity of a disease associated with metabolic syndrome and/or other metabolic diseases and disorders described herein that are associated with or related to metabolic syndrome. Optimal doses and the frequency of dose delivery may generally be determined using experimental models and/or clinical trials. As described herein, the optimal dose may depend upon the body mass, weight, or blood volume of the patient and may vary from 1 ng/ml to 10 mg/ml, and may be administered daily or every other day, or three days, four days, five, or six days per week.

Any suitable pharmaceutical excipient or carrier known to those of ordinary skill in the art may be employed in the pharmaceutical compositions described herein. Excipients for therapeutic use are well known, and are described, for example, in *Remingtons Pharmaceutical Sciences*, Mack Publishing Co. (A. R. Gennaro ed. 1985). In general, the type of excipient is selected based on the mode of administration. Pharmaceutical compositions may be formulated for any appropriate manner of administration, including, for example, topical, oral, nasal, pulmonary, intraperitoneal, intrathecal, rectal, vaginal, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax, or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic.

The following Examples are offered by way of illustration and not by way of limitation.

EXAMPLES

Example 1

Desialylation of TSHR Polypeptide Agonists

This Example describes preparation of a substantially desialylated TSHR agonist. Recombinant human TSH (Thyrogen®, rhTSH, Genzyme, Cambridge, Mass.) is used as a starting material for the preparation of homogenous, desialylated TSH (asTSH). 300 μg of rhTSH is incubated with 40 mU *Vibrio cholerae* α2-3,6,8-neuraminidase conjugated to agarose beads (Calbiochem, San Diego, Calif.) in 50 mM sodium acetate, pH 5.5, and 1 mM $CaCl_2$ for 2 hours at 37° C. This results in complete removal of sialic acid without alterations to the remaining carbohydrate structure or peptide backbone. The reaction mixture is centrifuged to pellet the enzyme-conjugated agarose, and the supernatant filtered through a 60 kDa Centricon membrane (Amicon®, Millipore, Billerica, Mass.) to remove any free 90 kDa neuraminidase. A 10 kDa Amicon concentrator is used to remove free sialic acid and buffer exchange the asTSH into sterile saline. Protein concentration of the product is directly compared to the starting material because sialic acid does not absorb at 280 nm. SDS gel electrophoresis of the product is performed according to standard techniques to verify that the polypeptide backbone of the protein remains intact throughout the procedure.

Example 2

Treatment of Isolated Human Adipocytes with a TSHR Polypeptide Agonist

This example describes determination of the intrinsic activity a substantially desialylated TSHR agonist. In this example, the intrinsic activity of asTSH with rhTSH on human adipose tissue is compared. Cultured human adipocytes are treated with agonists and the lipolytic activity of the test materials is determined by the release of free fatty acids (FFA) into the conditioned medium. Lipolytic activity is the preferred measure of intrinsic activity in these experiments.

Human adipocytes are derived by isolation of preadipocytes, following collagenase digestion of subcutaneous fat tissue removed from a female patient undergoing elective surgery. The preadipocytes are differentiated into mature adipocytes by a commercial vendor (Zen-Bio, Research Triangle Park, N.C.) according to the vendor's protocol, and supplied in 96 well assay plates. After receipt, the adipocytes are maintained in medium supplied by the manufacturer for 5-7 days to complete the differentiation process and to allow accumulation of stored triglycerides.

Adipocytes are treated with dose ranges of 0.1-150 nM of asTSH and rhTSH and 1-1,000 nM Isoproterenol, a non-specific β-AR receptor agonist used as a positive control. The adipocytes are treated for 4 hours at 37° C., before the conditioned medium is harvested for assay.

Free fatty acids are measured using the Wako NEFA C kit (Wako Chemicals USA, Richmond, Va.) for quantitative determination of non-esterified (or free) fatty acids with a modified protocol (see U.S. Patent Application Publication No. 2004/0176294). Isoproterenol (MP Biomedicals, Irvine, Calif.), a lipolysis-inducing positive control, is diluted to a starting concentration of 2 μM in assay medium (Life Technologies low glucose DMEM, 1 mM sodium pyruvate, 2 mM L-glutamine, 20 mM HEPES, and 0.5% BSA) (Invitrogen Corporation, Carlsbad, Calif.). The isoproterenol is further diluted in half-log serial dilutions. TSHR agonists are serially diluted to 0.06 nM as the lowest concentration. Medium is removed from human adipocytes in 96-well plates. Fifty μl of assay medium is added to each well, followed by 50 μl of TSHR agonist or isoproterenol to each well. The plates are incubated for 4 hours at 37° C. 40 μl of conditioned medium are collected for glycerol assay analysis, and 40 μl of conditioned medium are collected for free fatty acid analysis.

Oleic acid (Sigma-Aldrich, St. Louis, Mo.) is dissolved in methanol and used as a reference for determining the amount of free fatty acids in the conditioned media. Wako reagents A and B are reconstituted to 4× the recommended concentration. Conditioned media samples are assayed in 96-well plates. 50 μl of Wako reagent A are added to 5 μl of oleic acid standard plus 40 μl of assay medium. 50 μl of Wako reagent A are added to 40 μl of conditioned medium from differentiated adipoctyes and 5 μl of methanol. The 96-well plates are incubated at 37° C. for 10 minutes. 100 μl of Wako reagent B are added to each well. The 96-well plates are incubated at 37° C. for 10 minutes. The 96-well plates are then allowed to sit at room temperature for 5 minutes. The 96-well plates are centrifuged in a Beckman Coulter Allegra 6R centrifuge at 3250×g for 5 minutes to remove air bubbles. The absorbance at 530 nm is measured on the Wallac Victor2 Multilabel counter. Released FFA from the test wells are determined by fitting to the oleic acid standard curve.

Potency of lipolytic stimulus produced by the TSHR agonists is determined by comparison to Isoproterenol. All three test agents release approximately equal amounts of FFA into the conditioned medium at maximum stimulation, and are equipotent lipolytic agents. Intrinsic activity of the TSHR agonists is determined by the $EC_{50}$ of lipolysis determined from the standard curve generated for each test material.

Example 3

Analysis of TSHR Agonist Glycoform in Non-Human Primates

The determination of parameters defining the therapeutic dose of TSHR agonist that is substantially desialylated is obtained from pharmacokinetic studies in Rhesus monkeys with a minimum body weight of 8 kg. The intrinsic activity is determined by the lipolytic potency of the agonist, and the serum clearance of the exogenously administered test TSHR agonist is determined following intramuscular (i.m.) injection. The extent of transient elevation in serum thyroid hormone levels is also determined.

Protocol

Four groups of 5 animals each are fasted overnight, and 3.5 mls of blood drawn to establish baseline values for various parameters. Animals in groups (1) vehicle; (2) 10 μg/kg asTSH (see Example 1); (3) 50 μg/kg asTSH; and (4) 50 μg/kg rhTSH are injected intramuscularly (i.m.) at time zero. Blood (3.5 mls) is withdrawn at 1 h, 3 h, 6 h, 8 h, 12 h, and 24 h timepoints. Glycerol levels in serum are determined as described in example 1 to measure lipolytic activity. Serum TSH and thyroid hormone levels are determined by immunometric assay according to the manufacturer's protocol (Biocheck, Foster City, Calif.). Previous studies have revealed that Rhesus monkey TSH (i.e., endogenous TSH) is not recognized by the immunometric assay for human TSH, thus all TSH measurements are for exogenously introduced TSH.

From the foregoing it will be appreciated that, although specific embodiments of the invention have been described herein for purposes of illustration, various modifications may be made without deviating from the spirit and scope of the invention. The invention is further described by the appended claims.

What is claimed is:

1. A method for inducing lipolysis in a human subject who has metabolic syndrome, comprising:

administering to the subject a composition that comprises (a) a thyroid-stimulating hormone receptor (TSHR) agonist preparation selected from (i) a recombinant human thyroid-stimulating hormone (TSH) preparation and (ii) a recombinant human corticotroph-derived glycoprotein hormone (CGH) preparation; and (b) a pharmaceutically acceptable carrier, wherein said TSHR agonist preparation is at least 90% desialylated, wherein the TSHR agonist preparation is administered in an amount effective to induce lipolysis in a plurality of adipocytes without inducing thyrotoxicosis in the subject.

2. The method of claim 1 wherein the TSH preparation lacks sialic acid.

3. The method of claim 1 wherein the TSHR agonist preparation is a recombinant human corticotroph-derived glycoprotein hormone (CGH) glycoprotein preparation that lacks sialic acid.

4. The method of claim 1 wherein metabolic syndrome comprises at least one metabolic disorder that is selected from obesity, type 2 diabetes mellitus, hyperlipidemia, insulin resistance, steatohepatitis, hypertension, and dyslipidemia.

5. The method of claim 1 wherein the subject (a) is obese; (b) has type 2 diabetes mellitus; or (c) is obese and has type 2 diabetes mellitus.

6. A method of altering a metabolic activity in a human subject, comprising:

administering to the subject a composition that comprises (a) a thyroid-stimulating hormone receptor (TSHR) agonist preparation selected from (i) a recombinant human thyroid-stimulating hormone (TSH) preparation and (ii) a recombinant human corticotroph-derived glycoprotein hormone (CGH) preparation; and (b) a pharmaceutically acceptable carrier, wherein said TSHR agonist preparation is at least 90% desialylated, wherein the altering of the metabolic activity is inducing lipolysis in adipocytes in the subject, and wherein the TSHR agonist preparation is administered in an amount sufficient to alter the metabolic activity.

7. The method of claim 6 wherein the TSHR agonist preparation is the recombinant human TSH preparation, wherein the preparation lacks sialic acid.

8. The method of claim 6 wherein the TSHR agonist preparation is the recombinant human CGH preparation, wherein the preparation lacks sialic acid.

* * * * *